(12) United States Patent
Goraltchouk et al.

(10) Patent No.: US 9,044,225 B1
(45) Date of Patent: Jun. 2, 2015

(54) COMPOSITE SELF-RETAINING SUTURES AND METHOD

(75) Inventors: Alexei Goraltchouk, Santa Barbara, CA (US); Alexander Naimagon, Richmond (CA); Gerald F. Cummings, Port Moody (CA); Lev Drubetsky, Coquitlam (CA); Robert A. Herrmann, Vancouver (CA)

(73) Assignee: Ethicon, Inc., Somerville, NJ (US)

( * ) Notice: Subject to any disclaimer, the term of this patent is extended or adjusted under 35 U.S.C. 154(b) by 730 days.

(21) Appl. No.: 13/349,231

(22) Filed: Jan. 12, 2012

Related U.S. Application Data

(63) Continuation of application No. 12/340,530, filed on Dec. 19, 2008, now Pat. No. 8,118,834.

(60) Provisional application No. 61/015,489, filed on Dec. 20, 2007.

(51) Int. Cl.
   *A61B 17/04* (2006.01)
   *A61B 17/06* (2006.01)
   *A61B 17/00* (2006.01)

(52) U.S. Cl.
   CPC . *A61B 17/06166* (2013.01); *A61B 2017/00858* (2013.01); *A61B 2017/06057* (2013.01); *A61B 2017/06176* (2013.01); *A61B 2017/00004* (2013.01)

(58) Field of Classification Search
   CPC ............. A61B 17/06; A61B 17/06166; A61B 2017/06176; A61B 2017/00526; A61B 2017/00867; A61B 2017/06057; A61B 2017/00004; A61B 2017/00792; A61B 2017/00858; A61B 2017/00871; A61B 2017/00995
   USPC ............................ 606/219, 228–232; 264/129
   See application file for complete search history.

(56) References Cited

U.S. PATENT DOCUMENTS

| | | |
|---|---|---|
| 709,392 A | 9/1902 | Brown |
| 733,723 A | 7/1903 | Lukens |
| 816,026 A | 3/1906 | Meier |
| 1,142,510 A | 6/1915 | Engle |
| 1,728,316 A | 9/1929 | Von Wachenfeldt |
| 1,886,721 A | 11/1932 | O'Brien |
| 2,094,578 A | 10/1937 | Blumenthal et al. |

(Continued)

FOREIGN PATENT DOCUMENTS

| | | |
|---|---|---|
| BE | 1014364 | 9/2003 |
| CA | 2309844 | 12/1996 |

(Continued)

OTHER PUBLICATIONS

US 6,447,535, (withdrawn).

(Continued)

*Primary Examiner* — Julian W Woo

(57) ABSTRACT

A self-retaining suture comprises a composite filament. The filament has retainers on the surface such that the filament can engage and retain tissue without knots. The filament comprises at least two materials having different properties. A surface material of the filament has properties which enhance the formation, elevation and/or deployment of the retainers. A core material of the filament has properties which enhance the tensile strength of the filament. The surgical filament is thin and flexible and may be used for suturing. Methods for manufacturing the filament and retainers are also described.

1 Claim, 7 Drawing Sheets

(56) References Cited

U.S. PATENT DOCUMENTS

| | | |
|---|---|---|
| 2,201,610 A | 5/1940 | Dawson, Jr. |
| 2,232,142 A | 2/1941 | Schumann |
| 2,254,620 A | 9/1941 | Miller |
| 2,347,956 A | 5/1944 | Lansing |
| 2,355,907 A | 8/1944 | Cox |
| 2,421,193 A | 5/1947 | Gardner |
| 2,452,734 A | 11/1948 | Costelow |
| 2,472,009 A | 5/1949 | Gardner |
| 2,480,271 A | 8/1949 | Sumner |
| 2,572,936 A | 10/1951 | Kulp et al. |
| 2,591,063 A | 4/1952 | Goldberg |
| 2,684,070 A | 7/1954 | Kelsey |
| 2,736,964 A | 3/1956 | Lieberman |
| 2,779,083 A | 1/1957 | Enton |
| 2,817,339 A | 12/1957 | Sullivan |
| 2,830,366 A | 4/1958 | Chisena |
| 2,866,256 A | 12/1958 | Matlin |
| 2,910,067 A | 10/1959 | White |
| 2,928,395 A | 3/1960 | Forbes et al. |
| 2,988,028 A | 6/1961 | Alcamo |
| 3,003,155 A | 10/1961 | Mielzynski et al. |
| 3,066,452 A | 12/1962 | Bott et al. |
| 3,066,673 A | 12/1962 | Bott et al. |
| 3,068,869 A | 12/1962 | Shelden et al. |
| 3,068,870 A | 12/1962 | Levin |
| 3,082,523 A | 3/1963 | Modes et al. |
| 3,123,077 A | 3/1964 | Alcamo |
| 3,166,072 A | 1/1965 | Sullivan, Jr. |
| 3,187,752 A | 6/1965 | Glick |
| 3,206,018 A | 9/1965 | Lewis et al. |
| 3,209,652 A | 10/1965 | Burgsmueller |
| 3,209,754 A | 10/1965 | Brown |
| 3,212,187 A | 10/1965 | Benedict |
| 3,214,810 A | 11/1965 | Mathison |
| 3,221,746 A | 12/1965 | Noble |
| 3,234,636 A | 2/1966 | Brown |
| 3,273,562 A | 9/1966 | Brown |
| 3,352,191 A | 11/1967 | Crawford |
| 3,378,010 A | 4/1968 | Codling |
| 3,385,299 A | 5/1968 | LeRoy |
| 3,494,006 A | 2/1970 | Brumlik |
| 3,522,637 A | 8/1970 | Brumlik |
| 3,525,340 A | 8/1970 | Gilbert |
| 3,545,608 A | 12/1970 | Berger et al. |
| 3,557,795 A | 1/1971 | Hirsch |
| 3,570,497 A | 3/1971 | Lemole |
| 3,586,002 A | 6/1971 | Wood |
| 3,608,095 A | 9/1971 | Barry |
| 3,608,539 A | 9/1971 | Miller |
| 3,618,447 A | 11/1971 | Goins |
| 3,646,615 A | 3/1972 | Ness |
| 3,683,926 A | 8/1972 | Suzuki |
| 3,716,058 A | 2/1973 | Tanner, Jr. |
| 3,720,055 A | 3/1973 | de Mestral et al. |
| 3,748,701 A | 7/1973 | De Mestral |
| 3,762,418 A | 10/1973 | Wasson |
| 3,825,010 A | 7/1974 | McDonald |
| 3,833,972 A | 9/1974 | Brumlik |
| 3,845,641 A | 11/1974 | Waller |
| 3,847,156 A | 11/1974 | Trumble |
| 3,889,322 A | 6/1975 | Brumlik |
| 3,918,455 A | 11/1975 | Coplan |
| 3,922,455 A | 11/1975 | Brumlik |
| 3,941,164 A | 3/1976 | Musgrave |
| 3,977,937 A | 8/1976 | Candor |
| 3,980,177 A | 9/1976 | McGregor |
| 3,981,051 A | 9/1976 | Brumlik |
| 3,981,307 A | 9/1976 | Borysko |
| 3,985,138 A | 10/1976 | Jarvik |
| 3,990,144 A | 11/1976 | Schwartz |
| 4,006,747 A | 2/1977 | Kronenthal |
| 4,008,303 A | 2/1977 | Glick et al. |
| 4,027,608 A | 6/1977 | Arbuckle |
| 4,043,344 A | 8/1977 | Landi et al. |
| 4,052,988 A | 10/1977 | Doddi et al. |
| D246,911 S | 1/1978 | Bess, Jr. et al. |
| 4,069,825 A | 1/1978 | Akiyama |
| 4,073,298 A | 2/1978 | Le Roy |
| 4,075,962 A | 2/1978 | Mabry |
| 4,098,210 A | 7/1978 | Wright |
| 4,137,921 A | 2/1979 | Okuzumi et al. |
| 4,182,340 A | 1/1980 | Spencer |
| 4,186,239 A | 1/1980 | Mize et al. |
| 4,198,734 A | 4/1980 | Brumlik |
| 4,204,541 A | 5/1980 | Kapitanov |
| 4,204,542 A | 5/1980 | Bokros et al. |
| 4,259,959 A | 4/1981 | Walker |
| 4,278,374 A | 7/1981 | Wolosianski |
| 4,300,424 A | 11/1981 | Flinn |
| 4,311,002 A | 1/1982 | Hoffmann et al. |
| 4,313,448 A | 2/1982 | Stokes |
| 4,316,469 A | 2/1982 | Kapitanov |
| 4,317,451 A | 3/1982 | Cerwin et al. |
| 4,372,293 A | 2/1983 | Vijil-Rosales |
| 4,428,376 A | 1/1984 | Mericle |
| 4,430,998 A | 2/1984 | Harvey |
| 4,434,796 A | 3/1984 | Karapetian |
| 4,449,298 A | 5/1984 | Patz |
| 4,454,875 A | 6/1984 | Pratt et al. |
| 4,467,805 A | 8/1984 | Fukuda |
| 4,490,326 A | 12/1984 | Beroff et al. |
| 4,492,075 A | 1/1985 | Faure |
| 4,493,323 A | 1/1985 | Albright et al. |
| 4,505,274 A | 3/1985 | Speelman |
| 4,510,934 A | 4/1985 | Batra |
| 4,531,522 A | 7/1985 | Bedi et al. |
| 4,532,926 A | 8/1985 | O'Holla |
| 4,535,772 A | 8/1985 | Sheehan |
| 4,548,202 A | 10/1985 | Duncan |
| 4,553,544 A | 11/1985 | Nomoto et al. |
| 4,610,250 A | 9/1986 | Green |
| 4,610,251 A | 9/1986 | Kumar |
| 4,635,637 A | 1/1987 | Schreiber |
| 4,637,380 A | 1/1987 | Orejola |
| 4,653,486 A | 3/1987 | Coker |
| 4,669,473 A | 6/1987 | Richards et al. |
| 4,676,245 A | 6/1987 | Fukuda |
| 4,689,882 A | 9/1987 | Lorenz |
| 4,702,250 A | 10/1987 | Ovil et al. |
| 4,712,553 A | 12/1987 | MacGregor |
| 4,719,917 A | 1/1988 | Barrows |
| 4,741,330 A | 5/1988 | Hayhurst |
| 4,750,910 A | 6/1988 | Takayanagi et al. |
| 4,776,337 A | 10/1988 | Palmaz |
| 4,832,025 A | 5/1989 | Coates |
| 4,841,960 A | 6/1989 | Garner |
| 4,865,026 A | 9/1989 | Barrett |
| 4,873,976 A | 10/1989 | Schreiber |
| 4,887,601 A | 12/1989 | Richards |
| 4,895,148 A | 1/1990 | Bays et al. |
| 4,898,156 A | 2/1990 | Gatturna et al. |
| 4,899,743 A | 2/1990 | Nicholson et al. |
| 4,900,605 A | 2/1990 | Thorgersen et al. |
| 4,905,367 A | 3/1990 | Pinchuk et al. |
| 4,930,945 A | 6/1990 | Arai et al. |
| 4,932,962 A | 6/1990 | Yoon et al. |
| 4,946,468 A | 8/1990 | Li |
| 4,948,444 A | 8/1990 | Schultz et al. |
| 4,950,258 A | 8/1990 | Kawai et al. |
| 4,950,285 A | 8/1990 | Wilk |
| 4,968,315 A | 11/1990 | Gatturna |
| 4,976,715 A | 12/1990 | Bays et al. |
| 4,979,956 A | 12/1990 | Silvestrini et al. |
| 4,981,149 A | 1/1991 | Yoon |
| 4,994,073 A | 2/1991 | Green |
| 4,994,084 A | 2/1991 | Brennan |
| 4,997,439 A | 3/1991 | Chen |
| 5,002,550 A | 3/1991 | Li |
| 5,002,562 A | 3/1991 | Oberlander |
| 5,007,921 A | 4/1991 | Brown |
| 5,007,922 A | 4/1991 | Chen et al. |
| 5,026,390 A | 6/1991 | Brown |
| 5,037,422 A | 8/1991 | Hayhurst et al. |
| 5,037,433 A | 8/1991 | Wilk et al. |

(56) References Cited

U.S. PATENT DOCUMENTS

| | | | |
|---|---|---|---|
| 5,041,129 | A | 8/1991 | Hayhurst et al. |
| 5,046,513 | A | 9/1991 | Gatturna et al. |
| 5,047,047 | A | 9/1991 | Yoon |
| 5,053,047 | A | 10/1991 | Yoon |
| 5,084,063 | A | 1/1992 | Korthoff |
| 5,089,010 | A | 2/1992 | Korthoff |
| 5,102,418 | A | 4/1992 | Granger et al. |
| 5,102,421 | A | 4/1992 | Anspach, Jr. |
| 5,103,073 | A | 4/1992 | Danilov et al. |
| 5,112,344 | A | 5/1992 | Petros |
| 5,123,911 | A | 6/1992 | Granger et al. |
| 5,123,913 | A | 6/1992 | Wilk et al. |
| 5,123,919 | A | 6/1992 | Sauter et al. |
| 5,127,413 | A | 7/1992 | Ebert |
| 5,133,738 | A | 7/1992 | Korthoff et al. |
| 5,141,520 | A | 8/1992 | Goble et al. |
| 5,147,382 | A | 9/1992 | Gertzman et al. |
| 5,156,615 | A | 10/1992 | Korthoff et al. |
| 5,156,788 | A | 10/1992 | Chesterfield et al. |
| 5,176,692 | A | 1/1993 | Wilk et al. |
| 5,179,964 | A | 1/1993 | Cook |
| 5,192,274 | A | 3/1993 | Bierman |
| 5,192,302 | A | 3/1993 | Kensey et al. |
| 5,192,303 | A | 3/1993 | Gatturna et al. |
| 5,197,597 | A | 3/1993 | Leary et al. |
| 5,201,326 | A | 4/1993 | Kubicki et al. |
| 5,207,679 | A | 5/1993 | Li |
| 5,207,694 | A | 5/1993 | Broome |
| 5,217,486 | A | 6/1993 | Rice et al. |
| 5,217,494 | A | 6/1993 | Coggins et al. |
| 5,222,508 | A | 6/1993 | Contarini |
| 5,222,976 | A | 6/1993 | Yoon |
| 5,224,946 | A | 7/1993 | Hayhurst et al. |
| 5,234,006 | A | 8/1993 | Eaton et al. |
| 5,242,457 | A | 9/1993 | Akopov et al. |
| 5,246,441 | A | 9/1993 | Ross et al. |
| 5,259,846 | A | 11/1993 | Granger et al. |
| 5,263,973 | A | 11/1993 | Cook |
| 5,269,783 | A | 12/1993 | Sander |
| 5,282,832 | A | 2/1994 | Toso et al. |
| 5,292,326 | A | 3/1994 | Green |
| 5,306,288 | A | 4/1994 | Granger et al. |
| 5,306,290 | A | 4/1994 | Martins et al. |
| 5,312,422 | A | 5/1994 | Trott |
| 5,320,629 | A | 6/1994 | Noda et al. |
| 5,330,488 | A | 7/1994 | Goldrath |
| 5,330,503 | A | 7/1994 | Yoon |
| 5,342,376 | A | 8/1994 | Ruff |
| 5,342,395 | A | 8/1994 | Jarrett et al. |
| 5,350,385 | A | 9/1994 | Christy |
| 5,352,515 | A | 10/1994 | Jarrett et al. |
| 5,354,271 | A | 10/1994 | Voda |
| 5,354,298 | A | 10/1994 | Lee et al. |
| 5,358,511 | A | 10/1994 | Gatturna et al. |
| 5,363,556 | A | 11/1994 | Banholzer et al. |
| 5,372,146 | A | 12/1994 | Branch |
| 5,374,268 | A | 12/1994 | Sander |
| 5,374,278 | A | 12/1994 | Chesterfield et al. |
| 5,380,334 | A | 1/1995 | Torrie et al. |
| 5,387,383 | A * | 2/1995 | Collier et al. ............... 264/129 |
| 5,391,173 | A | 2/1995 | Wilk |
| 5,403,346 | A | 4/1995 | Loeser |
| 5,411,523 | A | 5/1995 | Goble |
| 5,414,988 | A | 5/1995 | DiPalma et al. |
| 5,417,691 | A | 5/1995 | Hayhurst |
| 5,425,746 | A | 6/1995 | Proto et al. |
| 5,425,747 | A | 6/1995 | Brotz |
| 5,437,680 | A | 8/1995 | Yoon et al. |
| 5,450,860 | A | 9/1995 | O'Connor |
| 5,451,461 | A | 9/1995 | Broyer |
| 5,462,561 | A | 10/1995 | Voda |
| 5,464,422 | A | 11/1995 | Silverman |
| 5,464,426 | A | 11/1995 | Bonutti |
| 5,464,427 | A | 11/1995 | Curtis et al. |
| 5,472,452 | A | 12/1995 | Trott |
| 5,478,353 | A | 12/1995 | Yoon |
| 5,480,403 | A | 1/1996 | Lee et al. |
| 5,480,411 | A | 1/1996 | Liu et al. |
| 5,484,451 | A | 1/1996 | Akopov et al. |
| 5,486,197 | A | 1/1996 | Le et al. |
| 5,500,000 | A | 3/1996 | Feagin et al. |
| 5,500,991 | A | 3/1996 | Demarest et al. |
| 5,520,084 | A | 5/1996 | Chesterfield et al. |
| 5,520,691 | A | 5/1996 | Branch |
| 5,522,845 | A | 6/1996 | Wenstrom, Jr. |
| 5,527,342 | A | 6/1996 | Pietrzak et al. |
| 5,531,760 | A | 7/1996 | Alwafaie |
| 5,531,761 | A | 7/1996 | Yoon |
| 5,531,790 | A | 7/1996 | Frechet et al. |
| 5,536,582 | A | 7/1996 | Prasad et al. |
| 5,540,705 | A | 7/1996 | Meade et al. |
| 5,540,718 | A | 7/1996 | Bartlett |
| 5,545,148 | A | 8/1996 | Wurster |
| 5,549,631 | A | 8/1996 | Bonutti |
| 5,554,171 | A | 9/1996 | Gatturna et al. |
| 5,569,272 | A | 10/1996 | Reed et al. |
| 5,571,139 | A | 11/1996 | Jenkins, Jr. |
| 5,571,175 | A | 11/1996 | Vanney et al. |
| 5,571,216 | A | 11/1996 | Anderson |
| 5,573,543 | A | 11/1996 | Akopov et al. |
| 5,584,859 | A | 12/1996 | Brotz |
| 5,593,424 | A | 1/1997 | Northrup, III et al. |
| 5,601,557 | A | 2/1997 | Hayhurst |
| 5,626,590 | A | 5/1997 | Wilk |
| 5,626,611 | A | 5/1997 | Liu et al. |
| 5,632,753 | A | 5/1997 | Loeser |
| 5,643,288 | A | 7/1997 | Thompson |
| 5,643,295 | A | 7/1997 | Yoon |
| 5,643,319 | A | 7/1997 | Green et al. |
| 5,645,568 | A | 7/1997 | Chervitz et al. |
| 5,647,874 | A | 7/1997 | Hayhurst |
| 5,649,939 | A | 7/1997 | Reddick |
| 5,653,716 | A | 8/1997 | Malo et al. |
| 5,662,714 | A | 9/1997 | Charvin et al. |
| 5,669,935 | A | 9/1997 | Rosenman et al. |
| 5,676,675 | A | 10/1997 | Grice |
| D386,583 | S | 11/1997 | Ferragamo et al. |
| 5,683,417 | A | 11/1997 | Cooper |
| D387,161 | S | 12/1997 | Ferragamo et al. |
| 5,693,072 | A | 12/1997 | McIntosh |
| 5,695,879 | A | 12/1997 | Goldmann et al. |
| 5,697,976 | A | 12/1997 | Chesterfield et al. |
| 5,702,397 | A | 12/1997 | Goble et al. |
| 5,702,462 | A | 12/1997 | Oberlander |
| 5,709,692 | A | 1/1998 | Mollenauer et al. |
| 5,716,358 | A | 2/1998 | Ochoa et al. |
| 5,716,376 | A | 2/1998 | Roby et al. |
| 5,722,991 | A | 3/1998 | Colligan |
| 5,723,008 | A | 3/1998 | Gordon |
| 5,725,557 | A | 3/1998 | Gatturna et al. |
| 5,728,114 | A | 3/1998 | Evans et al. |
| 5,731,855 | A | 3/1998 | Koyama et al. |
| 5,741,277 | A | 4/1998 | Gordon et al. |
| 5,744,151 | A | 4/1998 | Capelli |
| 5,763,411 | A | 6/1998 | Edwardson et al. |
| 5,765,560 | A | 6/1998 | Verkerke et al. |
| 5,766,246 | A | 6/1998 | Mulhauser et al. |
| 5,779,719 | A | 7/1998 | Klein et al. |
| 5,782,864 | A | 7/1998 | Lizardi |
| 5,807,403 | A | 9/1998 | Beyar et al. |
| 5,807,406 | A | 9/1998 | Brauker et al. |
| 5,810,853 | A | 9/1998 | Yoon |
| 5,814,051 | A | 9/1998 | Wenstrom, Jr. |
| 5,843,087 | A | 12/1998 | Jensen et al. |
| 5,843,178 | A | 12/1998 | Vanney et al. |
| 5,855,619 | A | 1/1999 | Caplan et al. |
| 5,863,360 | A | 1/1999 | Wood et al. |
| 5,887,594 | A | 3/1999 | LoCicero, III |
| 5,891,166 | A | 4/1999 | Schervinsky |
| 5,893,856 | A | 4/1999 | Jacob et al. |
| 5,895,395 | A | 4/1999 | Yeung |
| 5,895,413 | A | 4/1999 | Nordstrom |
| 5,897,572 | A | 4/1999 | Schulsinger et al. |
| 5,899,911 | A | 5/1999 | Carter |

(56) References Cited

U.S. PATENT DOCUMENTS

| | | |
|---|---|---|
| 5,916,224 A | 6/1999 | Esplin |
| 5,919,234 A | 7/1999 | Lemperle et al. |
| 5,925,078 A | 7/1999 | Anderson |
| 5,931,855 A | 8/1999 | Buncke |
| 5,938,668 A | 8/1999 | Scirica et al. |
| 5,941,899 A | 8/1999 | Granger et al. |
| 5,950,633 A | 9/1999 | Lynch et al. |
| 5,954,747 A | 9/1999 | Clark |
| 5,964,765 A | 10/1999 | Fenton, Jr. et al. |
| 5,964,783 A | 10/1999 | Grafton et al. |
| 5,968,097 A | 10/1999 | Frechet et al. |
| 5,972,024 A | 10/1999 | Northrup, III et al. |
| 5,984,933 A | 11/1999 | Yoon |
| 5,993,459 A | 11/1999 | Larsen et al. |
| 5,997,554 A | 12/1999 | Thompson |
| 6,001,111 A | 12/1999 | Sepetka et al. |
| 6,012,216 A | 1/2000 | Esteves et al. |
| 6,015,410 A | 1/2000 | Tormala et al. |
| 6,024,757 A | 2/2000 | Haase et al. |
| 6,027,523 A | 2/2000 | Schmieding |
| 6,039,741 A | 3/2000 | Meislin |
| 6,042,583 A | 3/2000 | Thompson et al. |
| 6,045,571 A | 4/2000 | Hill et al. |
| 6,056,778 A | 5/2000 | Grafton et al. |
| 6,063,105 A | 5/2000 | Totakura |
| 6,071,292 A | 6/2000 | Makower et al. |
| 6,074,419 A | 6/2000 | Healy et al. |
| 6,076,255 A | 6/2000 | Shikakubo et al. |
| 6,083,244 A | 7/2000 | Lubbers et al. |
| 6,102,947 A | 8/2000 | Gordon |
| 6,106,544 A | 8/2000 | Brazeau |
| 6,106,545 A | 8/2000 | Egan |
| 6,110,484 A | 8/2000 | Sierra |
| 6,129,741 A | 10/2000 | Wurster et al. |
| D433,753 S | 11/2000 | Weiss |
| 6,146,406 A | 11/2000 | Shluzas et al. |
| 6,146,407 A | 11/2000 | Krebs |
| 6,149,660 A | 11/2000 | Laufer et al. |
| 6,159,234 A | 12/2000 | Bonutti et al. |
| 6,160,084 A | 12/2000 | Langer et al. |
| 6,163,948 A | 12/2000 | Esteves et al. |
| 6,165,203 A | 12/2000 | Krebs |
| 6,168,633 B1 | 1/2001 | Shoher et al. |
| 6,174,324 B1 | 1/2001 | Egan et al. |
| 6,183,499 B1 | 2/2001 | Fischer et al. |
| 6,187,095 B1 | 2/2001 | Labrecque et al. |
| 6,203,565 B1 | 3/2001 | Bonutti et al. |
| 6,206,908 B1 | 3/2001 | Roby |
| 6,214,030 B1 | 4/2001 | Matsutani et al. |
| 6,231,911 B1 | 5/2001 | Steinback et al. |
| 6,235,869 B1 | 5/2001 | Roby et al. |
| 6,241,747 B1 | 6/2001 | Ruff |
| 6,251,143 B1 | 6/2001 | Schwartz et al. |
| 6,264,675 B1 | 7/2001 | Brotz |
| 6,267,772 B1 | 7/2001 | Mulhauser et al. |
| 6,270,517 B1 | 8/2001 | Brotz |
| 6,315,788 B1 | 11/2001 | Roby |
| 6,319,231 B1 | 11/2001 | Andrulitis |
| 6,322,581 B1 | 11/2001 | Fukuda et al. |
| 6,334,865 B1 | 1/2002 | Redmond et al. |
| 6,383,201 B1 | 5/2002 | Dong |
| 6,387,363 B1 | 5/2002 | Gruskin |
| 6,388,043 B1 | 5/2002 | Langer et al. |
| 6,395,029 B1 | 5/2002 | Levy |
| D462,766 S | 9/2002 | Jacobs et al. |
| 6,443,962 B1 | 9/2002 | Gaber |
| 6,471,715 B1 | 10/2002 | Weiss |
| 6,478,809 B1 | 11/2002 | Brotz |
| 6,485,503 B2 | 11/2002 | Jacobs et al. |
| 6,491,701 B2 | 12/2002 | Tierney et al. |
| 6,491,714 B1 | 12/2002 | Bennett |
| 6,494,898 B1 | 12/2002 | Roby et al. |
| 6,495,127 B1 | 12/2002 | Wallace et al. |
| RE37,963 E | 1/2003 | Thal |
| 6,506,190 B1 | 1/2003 | Walshe |
| 6,506,197 B1 | 1/2003 | Rollero et al. |
| 6,511,488 B1 | 1/2003 | Marshall et al. |
| 6,514,265 B2 | 2/2003 | Ho et al. |
| 6,527,795 B1 | 3/2003 | Lizardi |
| 6,548,002 B2 | 4/2003 | Gresser et al. |
| 6,548,569 B1 | 4/2003 | Williams et al. |
| 6,551,343 B1 | 4/2003 | Tormala et al. |
| 6,554,802 B1 | 4/2003 | Pearson et al. |
| 6,565,597 B1 | 5/2003 | Fearnot et al. |
| 6,592,609 B1 | 7/2003 | Bonutti |
| 6,596,296 B1 | 7/2003 | Nelson et al. |
| 6,599,310 B2 | 7/2003 | Leung et al. |
| 6,607,541 B1 | 8/2003 | Gardiner et al. |
| 6,610,078 B1 | 8/2003 | Bru-Magniez et al. |
| 6,613,059 B2 | 9/2003 | Schaller et al. |
| 6,613,254 B1 | 9/2003 | Shiffer |
| 6,616,982 B2 | 9/2003 | Merrill et al. |
| 6,623,492 B1 | 9/2003 | Berube et al. |
| 6,626,930 B1 | 9/2003 | Allen et al. |
| 6,632,245 B2 | 10/2003 | Kim |
| 6,641,592 B1 | 11/2003 | Sauer et al. |
| 6,641,593 B1 | 11/2003 | Schaller et al. |
| 6,645,226 B1 | 11/2003 | Jacobs et al. |
| 6,645,227 B2 | 11/2003 | Fallin et al. |
| 6,648,921 B2 | 11/2003 | Anderson et al. |
| 6,656,182 B1 | 12/2003 | Hayhurst |
| 6,689,153 B1 | 2/2004 | Skiba |
| 6,689,166 B2 | 2/2004 | Laurencin et al. |
| 6,692,761 B2 | 2/2004 | Mahmood et al. |
| 6,702,844 B1 | 3/2004 | Lazarus |
| 6,712,830 B2 | 3/2004 | Esplin |
| 6,712,859 B2 | 3/2004 | Rousseau et al. |
| 6,716,234 B2 | 4/2004 | Grafton et al. |
| 6,720,402 B2 | 4/2004 | Langer et al. |
| 6,726,705 B2 | 4/2004 | Peterson et al. |
| 6,746,443 B1 | 6/2004 | Morley et al. |
| 6,746,458 B1 | 6/2004 | Cloud |
| 6,749,616 B1 | 6/2004 | Nath |
| 6,773,450 B2 | 8/2004 | Leung et al. |
| 6,783,554 B2 | 8/2004 | Amara et al. |
| 6,814,748 B1 | 11/2004 | Baker et al. |
| 6,818,010 B2 | 11/2004 | Eichhorn et al. |
| 6,838,493 B2 | 1/2005 | Williams et al. |
| 6,848,152 B2 | 2/2005 | Genova et al. |
| 6,852,825 B2 | 2/2005 | Lendlein et al. |
| 6,860,891 B2 | 3/2005 | Schulze |
| 6,860,901 B1 | 3/2005 | Baker et al. |
| 6,867,248 B1 | 3/2005 | Martin et al. |
| 6,877,934 B2 | 4/2005 | Gainer |
| 6,881,766 B2 | 4/2005 | Hain |
| 6,893,452 B2 | 5/2005 | Jacobs |
| 6,905,484 B2 | 6/2005 | Buckman et al. |
| 6,911,035 B1 | 6/2005 | Blomme |
| 6,911,037 B2 | 6/2005 | Gainor et al. |
| 6,913,607 B2 | 7/2005 | Ainsworth et al. |
| 6,921,811 B2 | 7/2005 | Zamora et al. |
| 6,923,819 B2 | 8/2005 | Meade et al. |
| 6,945,021 B2 | 9/2005 | Michel |
| 6,945,980 B2 | 9/2005 | Nguyen et al. |
| 6,960,221 B2 | 11/2005 | Ho et al. |
| 6,960,233 B1 | 11/2005 | Berg et al. |
| 6,974,450 B2 | 12/2005 | Weber et al. |
| 6,981,983 B1 | 1/2006 | Rosenblatt et al. |
| 6,984,241 B2 | 1/2006 | Lubbers et al. |
| 6,986,780 B2 | 1/2006 | Rudnick et al. |
| 6,991,643 B2 | 1/2006 | Saadat |
| 6,996,880 B2 | 2/2006 | Kurtz, Jr. |
| 7,021,316 B2 | 4/2006 | Leiboff |
| 7,033,379 B2 | 4/2006 | Peterson |
| 7,037,984 B2 | 5/2006 | Lendlein et al. |
| 7,048,748 B1 | 5/2006 | Ustuner |
| 7,056,331 B2 | 6/2006 | Kaplan et al. |
| 7,056,333 B2 | 6/2006 | Walshe |
| 7,057,135 B2 | 6/2006 | Li |
| 7,063,716 B2 | 6/2006 | Cunningham |
| 7,070,610 B2 | 7/2006 | Im et al. |
| 7,081,135 B2 | 7/2006 | Smith et al. |
| 7,083,637 B1 | 8/2006 | Tannhauser |
| 7,083,648 B2 | 8/2006 | Yu et al. |

(56) References Cited

U.S. PATENT DOCUMENTS

| | | |
|---|---|---|
| 7,107,090 B2 | 9/2006 | Salisbury, Jr. et al. |
| 7,112,214 B2 | 9/2006 | Peterson et al. |
| 7,125,403 B2 | 10/2006 | Julian et al. |
| 7,125,413 B2 | 10/2006 | Grigoryants et al. |
| D532,107 S | 11/2006 | Peterson et al. |
| 7,138,441 B1 | 11/2006 | Zhang |
| 7,141,302 B2 | 11/2006 | Mueller et al. |
| 7,144,401 B2 | 12/2006 | Yamamoto et al. |
| 7,144,412 B2 | 12/2006 | Wolf et al. |
| 7,144,415 B2 | 12/2006 | DelRio et al. |
| 7,150,757 B2 | 12/2006 | Fallin et al. |
| 7,156,858 B2 | 1/2007 | Schuldt-Hempe et al. |
| 7,156,862 B2 | 1/2007 | Jacobs et al. |
| 7,160,312 B2 | 1/2007 | Saadat |
| 7,166,570 B2 | 1/2007 | Hunter et al. |
| 7,172,595 B1 | 2/2007 | Goble |
| 7,172,615 B2 | 2/2007 | Morriss et al. |
| 7,186,262 B2 | 3/2007 | Saadat |
| 7,195,634 B2 | 3/2007 | Schmieding et al. |
| 7,211,088 B2 | 5/2007 | Grafton et al. |
| 7,214,230 B2 | 5/2007 | Brock et al. |
| 7,217,744 B2 | 5/2007 | Lendlein et al. |
| 7,225,512 B2 | 6/2007 | Genova et al. |
| 7,226,468 B2 | 6/2007 | Ruff |
| 7,232,447 B2 | 6/2007 | Gellman et al. |
| 7,244,270 B2 | 7/2007 | Lesh et al. |
| 7,279,612 B1 | 10/2007 | Heaton et al. |
| 7,297,142 B2 | 11/2007 | Brock |
| 7,322,105 B2 | 1/2008 | Lewis |
| 7,329,271 B2 | 2/2008 | Koyfman et al. |
| 7,371,253 B2 | 5/2008 | Leung et al. |
| 7,513,904 B2 | 4/2009 | Sulamanidze et al. |
| 7,582,105 B2 | 9/2009 | Kolster |
| 7,601,164 B2 | 10/2009 | Wu |
| 7,624,487 B2 | 12/2009 | Trull et al. |
| 7,645,293 B2 | 1/2010 | Martinek et al. |
| 7,806,908 B2 | 10/2010 | Ruff |
| 7,845,356 B2 | 12/2010 | Paraschac et al. |
| 7,857,829 B2 | 12/2010 | Kaplan et al. |
| 7,879,072 B2 | 2/2011 | Bonutti et al. |
| 7,919,112 B2 | 4/2011 | Pathak et al. |
| 8,118,834 B1 | 2/2012 | Goraltchouk et al. |
| 8,216,273 B1 | 7/2012 | Goraltchouk et al. |
| 8,226,684 B2 | 7/2012 | Nawrocki et al. |
| 8,246,652 B2 | 8/2012 | Ruff |
| 8,308,761 B2 | 11/2012 | Brailovski et al. |
| 8,460,338 B2 | 6/2013 | Goraltchouk et al. |
| 8,615,856 B1 | 12/2013 | Gelbart |
| 8,641,732 B1 | 2/2014 | Goraltchouk et al. |
| 8,652,170 B2 | 2/2014 | Leung et al. |
| 8,679,158 B2 | 3/2014 | Leung et al. |
| 2001/0011187 A1 | 8/2001 | Pavcnik et al. |
| 2001/0018592 A1 | 8/2001 | Schaller et al. |
| 2001/0018599 A1 | 8/2001 | D'Aversa et al. |
| 2001/0039450 A1 | 11/2001 | Pavcnik et al. |
| 2001/0051807 A1 | 12/2001 | Grafton |
| 2002/0007218 A1 | 1/2002 | Cauthen |
| 2002/0022861 A1 | 2/2002 | Jacobs et al. |
| 2002/0029011 A1 | 3/2002 | Dyer |
| 2002/0029066 A1 | 3/2002 | Foerster |
| 2002/0077448 A1 | 6/2002 | Antal et al. |
| 2002/0095164 A1 | 7/2002 | Andreas et al. |
| 2002/0099394 A1 | 7/2002 | Houser et al. |
| 2002/0111641 A1 | 8/2002 | Peterson et al. |
| 2002/0111688 A1 | 8/2002 | Cauthen |
| 2002/0138009 A1 | 9/2002 | Brockway et al. |
| 2002/0151932 A1 | 10/2002 | Bryant et al. |
| 2002/0151980 A1 | 10/2002 | Cauthen |
| 2002/0161168 A1 | 10/2002 | Shalaby et al. |
| 2002/0165555 A1 | 11/2002 | Stein et al. |
| 2002/0173822 A1 | 11/2002 | Justin et al. |
| 2002/0179718 A1 | 12/2002 | Murokh et al. |
| 2002/0198544 A1 | 12/2002 | Uflacker |
| 2003/0040795 A1 | 2/2003 | Elson et al. |
| 2003/0069602 A1 | 4/2003 | Jacobs et al. |
| 2003/0088270 A1 | 5/2003 | Lubbers et al. |
| 2003/0149447 A1 | 8/2003 | Morency |
| 2003/0158604 A1 | 8/2003 | Cauthen, III et al. |
| 2003/0167072 A1 | 9/2003 | Oberlander |
| 2003/0199923 A1 | 10/2003 | Khairkhahan et al. |
| 2003/0203003 A1 | 10/2003 | Nelson et al. |
| 2003/0204193 A1 | 10/2003 | Gabriel et al. |
| 2003/0204195 A1 | 10/2003 | Keane et al. |
| 2003/0225424 A1 | 12/2003 | Benderev |
| 2003/0229361 A1 | 12/2003 | Jackson |
| 2003/0236551 A1 | 12/2003 | Peterson |
| 2004/0006353 A1 | 1/2004 | Bosley, Jr. et al. |
| 2004/0010275 A1 | 1/2004 | Jacobs et al. |
| 2004/0010276 A1 | 1/2004 | Jacobs et al. |
| 2004/0015187 A1 | 1/2004 | Lendlein et al. |
| 2004/0024169 A1 | 2/2004 | Shalaby et al. |
| 2004/0024420 A1 | 2/2004 | Lubbers et al. |
| 2004/0030354 A1 | 2/2004 | Leung et al. |
| 2004/0039415 A1 | 2/2004 | Zamierowski |
| 2004/0049224 A1 | 3/2004 | Buehlmann et al. |
| 2004/0059370 A1 | 3/2004 | Greene, Jr. et al. |
| 2004/0059377 A1 | 3/2004 | Peterson et al. |
| 2004/0060409 A1 | 4/2004 | Leung et al. |
| 2004/0060410 A1 | 4/2004 | Leung et al. |
| 2004/0068293 A1 | 4/2004 | Scalzo et al. |
| 2004/0068294 A1 | 4/2004 | Scalzo et al. |
| 2004/0088003 A1 | 5/2004 | Leung et al. |
| 2004/0093023 A1 | 5/2004 | Allen et al. |
| 2004/0098051 A1 | 5/2004 | Fallin et al. |
| 2004/0106949 A1 | 6/2004 | Cohn et al. |
| 2004/0116620 A1 | 6/2004 | Shalaby et al. |
| 2004/0138683 A1 | 7/2004 | Shelton et al. |
| 2004/0153153 A1 | 8/2004 | Elson et al. |
| 2004/0167572 A1 | 8/2004 | Roth et al. |
| 2004/0167575 A1 | 8/2004 | Roby |
| 2004/0186487 A1 | 9/2004 | Klein et al. |
| 2004/0193191 A1 | 9/2004 | Starksen et al. |
| 2004/0193217 A1 | 9/2004 | Lubbers et al. |
| 2004/0193257 A1 | 9/2004 | Wu et al. |
| 2004/0230223 A1 | 11/2004 | Bonutti et al. |
| 2004/0260340 A1 | 12/2004 | Jacobs et al. |
| 2004/0265282 A1 | 12/2004 | Wright et al. |
| 2004/0267309 A1 | 12/2004 | Garvin |
| 2005/0004601 A1 | 1/2005 | Kong et al. |
| 2005/0004602 A1 | 1/2005 | Hart et al. |
| 2005/0033324 A1 | 2/2005 | Phan |
| 2005/0034431 A1 | 2/2005 | Dey et al. |
| 2005/0038472 A1 | 2/2005 | Furst |
| 2005/0049636 A1 | 3/2005 | Leiboff |
| 2005/0055051 A1 | 3/2005 | Grafton |
| 2005/0059984 A1 | 3/2005 | Chanduszko et al. |
| 2005/0065533 A1 | 3/2005 | Magen et al. |
| 2005/0070959 A1 | 3/2005 | Cichocki, Jr. |
| 2005/0080455 A1 | 4/2005 | Schmieding et al. |
| 2005/0085857 A1 | 4/2005 | Peterson et al. |
| 2005/0096698 A1 | 5/2005 | Lederman |
| 2005/0113936 A1 | 5/2005 | Brustad et al. |
| 2005/0119694 A1 | 6/2005 | Jacobs et al. |
| 2005/0125020 A1 | 6/2005 | Meade et al. |
| 2005/0125034 A1 | 6/2005 | Cichocki, Jr. |
| 2005/0125035 A1 | 6/2005 | Cichocki, Jr. |
| 2005/0149064 A1 | 7/2005 | Peterson et al. |
| 2005/0149118 A1 | 7/2005 | Koyfman et al. |
| 2005/0154255 A1 | 7/2005 | Jacobs |
| 2005/0171561 A1 | 8/2005 | Songer et al. |
| 2005/0177190 A1 | 8/2005 | Zamierowski |
| 2005/0181009 A1 | 8/2005 | Hunter et al. |
| 2005/0182444 A1 | 8/2005 | Peterson et al. |
| 2005/0182445 A1 | 8/2005 | Zamierowski |
| 2005/0186247 A1 | 8/2005 | Hunter et al. |
| 2005/0197699 A1 | 9/2005 | Jacobs et al. |
| 2005/0199249 A1 | 9/2005 | Karram |
| 2005/0203576 A1 | 9/2005 | Sulamanidze et al. |
| 2005/0209542 A1 | 9/2005 | Jacobs et al. |
| 2005/0209612 A1 | 9/2005 | Nakao |
| 2005/0234510 A1 | 10/2005 | Zamierowski |
| 2005/0240220 A1 | 10/2005 | Zamierowski |
| 2005/0267531 A1 | 12/2005 | Ruff et al. |
| 2005/0267532 A1 | 12/2005 | Wu |

(56) References Cited

U.S. PATENT DOCUMENTS

| | | |
|---|---|---|
| 2005/0277984 A1 | 12/2005 | Long |
| 2005/0283246 A1 | 12/2005 | Cauthen, III et al. |
| 2006/0020272 A1 | 1/2006 | Gildenberg |
| 2006/0030884 A1 | 2/2006 | Yoeung et al. |
| 2006/0036266 A1 | 2/2006 | Sulamanidze et al. |
| 2006/0058470 A1 | 3/2006 | Rizk |
| 2006/0058574 A1 | 3/2006 | Priewe et al. |
| 2006/0058799 A1 | 3/2006 | Elson et al. |
| 2006/0058844 A1 | 3/2006 | White et al. |
| 2006/0063476 A1 | 3/2006 | Dore |
| 2006/0064115 A1 | 3/2006 | Allen et al. |
| 2006/0064116 A1 | 3/2006 | Allen et al. |
| 2006/0064127 A1 | 3/2006 | Fallin et al. |
| 2006/0079469 A1 | 4/2006 | Anderson et al. |
| 2006/0079935 A1 | 4/2006 | Kolster |
| 2006/0085016 A1 | 4/2006 | Eremia |
| 2006/0089525 A1 | 4/2006 | Mamo et al. |
| 2006/0089672 A1 | 4/2006 | Martinek |
| 2006/0111734 A1 | 5/2006 | Kaplan et al. |
| 2006/0111742 A1 | 5/2006 | Kaplan et al. |
| 2006/0116503 A1 | 6/2006 | Lendlein et al. |
| 2006/0122608 A1 | 6/2006 | Fallin et al. |
| 2006/0135994 A1 | 6/2006 | Ruff |
| 2006/0135995 A1 | 6/2006 | Ruff |
| 2006/0140999 A1 | 6/2006 | Lendlein et al. |
| 2006/0142784 A1 | 6/2006 | Kontos |
| 2006/0193769 A1 | 8/2006 | Nelson et al. |
| 2006/0194721 A1 | 8/2006 | Allen |
| 2006/0200062 A1 | 9/2006 | Saadat |
| 2006/0207612 A1 | 9/2006 | Jackson et al. |
| 2006/0229671 A1 | 10/2006 | Steiner et al. |
| 2006/0235445 A1 | 10/2006 | Birk et al. |
| 2006/0235447 A1 | 10/2006 | Walshe |
| 2006/0235516 A1 | 10/2006 | Cavazzoni |
| 2006/0241658 A1 | 10/2006 | Cerundolo |
| 2006/0249405 A1 | 11/2006 | Cerwin et al. |
| 2006/0253126 A1 | 11/2006 | Bjerken et al. |
| 2006/0257629 A1 | 11/2006 | Ledlein et al. |
| 2006/0258938 A1 | 11/2006 | Hoffman et al. |
| 2006/0272979 A1 | 12/2006 | Lubbers et al. |
| 2006/0276808 A1 | 12/2006 | Arnal et al. |
| 2006/0282099 A1 | 12/2006 | Stokes et al. |
| 2006/0286289 A1 | 12/2006 | Prajapati et al. |
| 2006/0287675 A1 | 12/2006 | Prajapati et al. |
| 2006/0287676 A1 | 12/2006 | Prajapati et al. |
| 2006/0293710 A1 | 12/2006 | Foerster et al. |
| 2007/0005109 A1 | 1/2007 | Popadiuk et al. |
| 2007/0005110 A1 | 1/2007 | Collier et al. |
| 2007/0016251 A1 | 1/2007 | Roby |
| 2007/0021779 A1 | 1/2007 | Garvin et al. |
| 2007/0027475 A1 | 2/2007 | Pagedas |
| 2007/0038249 A1 | 2/2007 | Kolster |
| 2007/0065663 A1 | 3/2007 | Trull et al. |
| 2007/0088135 A1 | 4/2007 | Lendlein et al. |
| 2007/0088391 A1 | 4/2007 | McAlexander et al. |
| 2007/0134292 A1 | 6/2007 | Suokas et al. |
| 2007/0135840 A1 | 6/2007 | Schmieding |
| 2007/0135843 A1 | 6/2007 | Burkhart |
| 2007/0151961 A1 | 7/2007 | Kleine et al. |
| 2007/0156175 A1 | 7/2007 | Weadock et al. |
| 2007/0167958 A1 | 7/2007 | Sulamanidze et al. |
| 2007/0185494 A1 | 8/2007 | Reese |
| 2007/0187861 A1 | 8/2007 | Geneva et al. |
| 2007/0208355 A1 | 9/2007 | Ruff |
| 2007/0208377 A1 | 9/2007 | Kaplan et al. |
| 2007/0213770 A1 | 9/2007 | Dreyfuss |
| 2007/0219587 A1 | 9/2007 | Accardo |
| 2007/0224237 A1 | 9/2007 | Hwang et al. |
| 2007/0225642 A1 | 9/2007 | Houser et al. |
| 2007/0225761 A1 | 9/2007 | Shetty |
| 2007/0225763 A1 | 9/2007 | Zwolinski et al. |
| 2007/0225764 A1 | 9/2007 | Benavitz et al. |
| 2007/0233188 A1 | 10/2007 | Hunt et al. |
| 2007/0239206 A1 | 10/2007 | Shelton, IV et al. |
| 2007/0239207 A1 | 10/2007 | Beramendi |
| 2007/0257395 A1 | 11/2007 | Lindh et al. |
| 2007/0282247 A1 | 12/2007 | Desai et al. |
| 2007/0293892 A1 | 12/2007 | Takasu |
| 2008/0004490 A1 | 1/2008 | Bosley, Jr. et al. |
| 2008/0004603 A1 | 1/2008 | Larkin et al. |
| 2008/0009838 A1 | 1/2008 | Schena et al. |
| 2008/0009888 A1 | 1/2008 | Ewers et al. |
| 2008/0009902 A1 | 1/2008 | Hunter et al. |
| 2008/0027273 A1 | 1/2008 | Gutterman |
| 2008/0027486 A1 | 1/2008 | Jones et al. |
| 2008/0046094 A1 | 2/2008 | Han et al. |
| 2008/0058869 A1 | 3/2008 | Stopek et al. |
| 2008/0064839 A1 | 3/2008 | Hadba et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2008/0077181 A1 | 3/2008 | Jones et al. |
| 2008/0082113 A1 | 4/2008 | Bishop et al. |
| 2008/0082129 A1 | 4/2008 | Jones et al. |
| 2008/0086169 A1 | 4/2008 | Jones et al. |
| 2008/0086170 A1 | 4/2008 | Jones et al. |
| 2008/0109036 A1 | 5/2008 | Stopek et al. |
| 2008/0131692 A1 | 6/2008 | Rolland et al. |
| 2008/0132943 A1 | 6/2008 | Maiorino et al. |
| 2008/0169059 A1 | 7/2008 | Messersmith et al. |
| 2008/0195147 A1 | 8/2008 | Stopek |
| 2008/0208358 A1 | 8/2008 | Bellamkonda et al. |
| 2008/0215072 A1 | 9/2008 | Kelly |
| 2008/0221618 A1 | 9/2008 | Chen et al. |
| 2008/0234731 A1 | 9/2008 | Leung et al. |
| 2008/0248216 A1 | 10/2008 | Yeung et al. |
| 2008/0255611 A1 | 10/2008 | Hunter |
| 2008/0255612 A1 | 10/2008 | Hunter |
| 2008/0262542 A1 | 10/2008 | Sulamanidze et al. |
| 2008/0281338 A1 | 11/2008 | Wohlert et al. |
| 2008/0281357 A1 | 11/2008 | Sung et al. |
| 2008/0312688 A1 | 12/2008 | Naworocki et al. |
| 2009/0012560 A1 | 1/2009 | Hunter et al. |
| 2009/0018577 A1 | 1/2009 | Leung et al. |
| 2009/0043336 A1 | 2/2009 | Yuan et al. |
| 2009/0076543 A1 | 3/2009 | Maiorino et al. |
| 2009/0082856 A1 | 3/2009 | Flanagan |
| 2009/0088835 A1 | 4/2009 | Wang |
| 2009/0099597 A1 | 4/2009 | Isse |
| 2009/0105753 A1 | 4/2009 | Greenhalgh et al. |
| 2009/0107965 A1 | 4/2009 | D'Agostino |
| 2009/0112236 A1 | 4/2009 | Stopek |
| 2009/0112259 A1 | 4/2009 | D'Agostino |
| 2009/0143819 A1 | 6/2009 | D'Agostino |
| 2009/0200487 A1 | 8/2009 | Maiorino et al. |
| 2009/0210006 A1 | 8/2009 | Cohen et al. |
| 2009/0216253 A1 | 8/2009 | Bell et al. |
| 2009/0226500 A1 | 9/2009 | Avelar et al. |
| 2009/0228021 A1 | 9/2009 | Leung |
| 2009/0248066 A1 | 10/2009 | Wilkie |
| 2009/0248067 A1 | 10/2009 | Maiorino |
| 2009/0248070 A1 | 10/2009 | Kosa et al. |
| 2009/0250588 A1 | 10/2009 | Robeson et al. |
| 2009/0259233 A1 | 10/2009 | Bogart et al. |
| 2009/0259251 A1 | 10/2009 | Cohen |
| 2009/0287245 A1 | 11/2009 | Ostrovsky et al. |
| 2009/0299407 A1 | 12/2009 | Yuan et al. |
| 2009/0299408 A1 | 12/2009 | Schuldt-Hempe et al. |
| 2009/0306710 A1 | 12/2009 | Lindh et al. |
| 2009/0318958 A1 | 12/2009 | Ochiai |
| 2010/0021516 A1 | 1/2010 | McKay |
| 2010/0023055 A1 | 1/2010 | Rousseau |
| 2010/0057123 A1 | 3/2010 | D'Agostino et al. |
| 2010/0063540 A1 | 3/2010 | Maiorino |
| 2010/0071833 A1 | 3/2010 | Maiorino |
| 2010/0087855 A1 | 4/2010 | Leung et al. |
| 2010/0101707 A1 | 4/2010 | Maiorino et al. |
| 2010/0160961 A1 | 6/2010 | Nawrocki et al. |
| 2010/0163056 A1 | 7/2010 | Tschopp et al. |
| 2010/0198257 A1 | 8/2010 | Stopek et al. |
| 2010/0211097 A1 | 8/2010 | Hadba et al. |
| 2010/0211098 A1 | 8/2010 | Hadba et al. |
| 2010/0230300 A1 | 9/2010 | Hunter et al. |

(56) References Cited

U.S. PATENT DOCUMENTS

| | | |
|---|---|---|
| 2010/0239635 A1 | 9/2010 | McClain et al. |
| 2010/0292718 A1 | 11/2010 | Sholev et al. |
| 2010/0294103 A1 | 11/2010 | Genova et al. |
| 2010/0294104 A1 | 11/2010 | Genova et al. |
| 2010/0294105 A1 | 11/2010 | Genova et al. |
| 2010/0294106 A1 | 11/2010 | Genova et al. |
| 2010/0294107 A1 | 11/2010 | Genova et al. |
| 2010/0298637 A1 | 11/2010 | Ruff |
| 2010/0298639 A1 | 11/2010 | Leung et al. |
| 2010/0298848 A1 | 11/2010 | Leung et al. |
| 2010/0298867 A1 | 11/2010 | Ruff |
| 2010/0298868 A1 | 11/2010 | Ruff |
| 2010/0298871 A1 | 11/2010 | Ruff et al. |
| 2010/0298874 A1 | 11/2010 | Leung et al. |
| 2010/0298875 A1 | 11/2010 | Leung et al. |
| 2010/0298876 A1 | 11/2010 | Leung et al. |
| 2010/0298878 A1 | 11/2010 | Leung et al. |
| 2010/0298879 A1 | 11/2010 | Leung et al. |
| 2010/0298880 A1 | 11/2010 | Leung et al. |
| 2010/0313723 A1 | 12/2010 | Genova et al. |
| 2010/0313729 A1 | 12/2010 | Genova et al. |
| 2010/0313730 A1 | 12/2010 | Genova et al. |
| 2010/0318122 A1 | 12/2010 | Leung et al. |
| 2010/0318123 A1 | 12/2010 | Leung et al. |
| 2010/0318124 A1 | 12/2010 | Leung et al. |
| 2011/0009902 A1 | 1/2011 | Leung et al. |
| 2011/0022086 A1 | 1/2011 | D'Agostino et al. |
| 2011/0046668 A1 | 2/2011 | Goraltchouk et al. |
| 2011/0046669 A1 | 2/2011 | Goraltchouk et al. |
| 2011/0093010 A1 | 4/2011 | Genova et al. |
| 2011/0106152 A1 | 5/2011 | Kozlowski |
| 2011/0125188 A1 | 5/2011 | Goraltchouk et al. |
| 2011/0130774 A1 | 6/2011 | Criscuolo et al. |
| 2011/0166597 A1 | 7/2011 | Herrmann et al. |
| 2011/0264138 A1 | 10/2011 | Avelar et al. |
| 2011/0288583 A1 | 11/2011 | Goraltchouk et al. |
| 2011/0319932 A1 | 12/2011 | Avelar et al. |
| 2012/0109188 A1 | 5/2012 | Viola |
| 2013/0165971 A1 | 6/2013 | Leung et al. |
| 2013/0172931 A1 | 7/2013 | Gross et al. |
| 2013/0180966 A1 | 7/2013 | Gross et al. |
| 2013/0204295 A1 | 8/2013 | Hunter et al. |
| 2013/0226234 A1 | 8/2013 | Avelar et al. |
| 2013/0238021 A1 | 9/2013 | Gross et al. |
| 2013/0238022 A1 | 9/2013 | Gross et al. |
| 2013/0245684 A1 | 9/2013 | Ruff et al. |
| 2013/0317545 A1 | 11/2013 | Gross et al. |

FOREIGN PATENT DOCUMENTS

| | | |
|---|---|---|
| CN | 2640420 | 9/2004 |
| DE | 01810800 | 6/1970 |
| DE | 03227984 | 2/1984 |
| DE | 04302895 | 8/1994 |
| DE | 19618891 | 4/1997 |
| DE | 19833703 | 2/2000 |
| DE | 10245025 | 4/2004 |
| DE | 102005004317 | 6/2006 |
| EP | 0121362 | 9/1987 |
| EP | 0329787 | 8/1989 |
| EP | 0513713 | 5/1992 |
| EP | 0428253 | 7/1994 |
| EP | 0632999 | 1/1995 |
| EP | 0513736 | 2/1995 |
| EP | 0464479 | 3/1995 |
| EP | 0464480 | 3/1995 |
| EP | 0576337 | 3/1997 |
| EP | 0574707 | 8/1997 |
| EP | 0612504 | 11/1997 |
| EP | 0558993 | 4/1998 |
| EP | 0913123 | 5/1999 |
| EP | 0916310 | 5/1999 |
| EP | 0664198 | 6/1999 |
| EP | 0960600 | 12/1999 |
| EP | 0705567 | 3/2002 |
| EP | 0673624 | 8/2002 |
| EP | 0839499 | 9/2003 |
| EP | 0755656 | 12/2003 |
| EP | 1075843 | 2/2005 |
| EP | 1525851 | 4/2005 |
| EP | 1532942 | 5/2005 |
| EP | 0826337 | 12/2005 |
| EP | 0991359 | 11/2007 |
| EP | 2036502 | 3/2009 |
| EP | 1948261 | 11/2010 |
| EP | 1726317 | 7/2012 |
| EP | 2338421 | 11/2012 |
| FR | 2619129 | 2/1989 |
| FR | 2693108 | 1/1994 |
| GB | 0267007 | 3/1927 |
| GB | 1091282 | 11/1967 |
| GB | 1428560 | 7/1973 |
| GB | 1506362 | 4/1978 |
| GB | 1508627 | 4/1978 |
| JP | 1506362 | 4/1978 |
| JP | 54-116419 | 9/1979 |
| JP | 63-288146 | 11/1988 |
| JP | 001113091 | 5/1989 |
| JP | 3-165751 | 7/1991 |
| JP | 4-096758 | 3/1992 |
| JP | 4-266749 | 9/1992 |
| JP | 9-103477 | 4/1997 |
| JP | 410085225 | 4/1998 |
| JP | 11-313826 | 11/1999 |
| JP | 011332828 | 12/1999 |
| JP | 2002-059235 | 2/2002 |
| JP | 2003-275217 | 9/2003 |
| JP | 2009-118967 | 6/2009 |
| KR | 10-2005-0072908 A | 7/2005 |
| KR | 6013299 | 2/2006 |
| NZ | 501224 | 3/2002 |
| NZ | 531262 | 12/2005 |
| RU | 2139690 | 10/1999 |
| RU | 2175855 | 11/2001 |
| RU | 2241389 | 12/2004 |
| RU | 2268752 | 1/2006 |
| SU | 1745214 | 7/1992 |
| SU | 1752358 | 8/1992 |
| WO | WO 96/06565 | 3/1966 |
| WO | WO 86/00020 | 1/1986 |
| WO | WO 87/01270 | 3/1987 |
| WO | WO 88/09157 | 12/1988 |
| WO | WO 89/05618 | 6/1989 |
| WO | WO 90/09149 | 8/1990 |
| WO | WO 90/14795 | 12/1990 |
| WO | WO 92/22336 | 12/1992 |
| WO | WO 95/16399 | 6/1995 |
| WO | WO 95/29637 | 11/1995 |
| WO | WO 98/52473 | 11/1998 |
| WO | WO 98/55031 | 12/1998 |
| WO | WO 99/21488 | 5/1999 |
| WO | WO 99/33401 | 7/1999 |
| WO | WO 99/52478 | 10/1999 |
| WO | WO 99/59477 | 11/1999 |
| WO | WO 99/62431 | 12/1999 |
| WO | WO 00/51658 | 9/2000 |
| WO | WO 00/51685 | 9/2000 |
| WO | WO 01/06952 | 2/2001 |
| WO | WO 01/56626 | 8/2001 |
| WO | WO 03/001979 | 1/2003 |
| WO | WO 03/003925 | 1/2003 |
| WO | WO 03/045255 | 6/2003 |
| WO | WO 03/077772 | 9/2003 |
| WO | WO 03/092758 | 11/2003 |
| WO | WO 03/103733 | 12/2003 |
| WO | WO 03/103972 | 12/2003 |
| WO | WO 03/105703 | 12/2003 |
| WO | WO 2004/014236 | 2/2004 |
| WO | WO 2004/030517 | 4/2004 |
| WO | WO 2004/030520 | 4/2004 |
| WO | WO 2004/030704 | 4/2004 |
| WO | WO 2004/030705 | 4/2004 |
| WO | WO 2004/062459 | 7/2004 |

(56) References Cited

FOREIGN PATENT DOCUMENTS

| WO | WO 2004/100801 | 11/2004 |
|---|---|---|
| WO | WO 2004/112853 | 12/2004 |
| WO | WO 2005/016176 | 2/2005 |
| WO | WO 2005/074913 | 8/2005 |
| WO | WO 2005/096955 | 10/2005 |
| WO | WO 2005/096956 | 10/2005 |
| WO | WO 2005/112787 | 12/2005 |
| WO | WO 2006/005144 | 1/2006 |
| WO | WO 2006/012128 | 2/2006 |
| WO | WO 2006/037399 | 4/2006 |
| WO | WO 2006/061868 | 6/2006 |
| WO | WO 2006/079469 | 8/2006 |
| WO | WO 2006/082060 | 8/2006 |
| WO | WO 2006/099703 | 9/2006 |
| WO | WO 2006/138300 | 12/2006 |
| WO | WO 2007/005291 | 1/2007 |
| WO | WO 2007/005296 | 1/2007 |
| WO | WO 2007/038837 | 4/2007 |
| WO | WO 2007/053812 | 5/2007 |
| WO | WO 2007/089864 | 8/2007 |
| WO | WO 2007/112024 | 10/2007 |
| WO | WO 2007/133103 | 11/2007 |
| WO | WO 2007/145614 | 12/2007 |
| WO | WO 2008/128113 | 10/2008 |
| WO | WO 2009/042841 | 4/2009 |
| WO | WO 2009/068252 | 6/2009 |
| WO | WO 2009/087105 | 7/2009 |
| WO | WO 2009/097556 | 8/2009 |
| WO | WO 2009/151876 | 12/2009 |
| WO | WO 2010/052007 | 5/2010 |
| WO | WO 2011/053375 | 5/2011 |
| WO | WO 2011/139916 | 11/2011 |
| WO | WO 2011/140283 | 11/2011 |

OTHER PUBLICATIONS

US 6,503,260, (withdrawn).
Bacci, Pier Antonio, "Chirurgia Estetica Mini Invasiva Con Fill Di Sostegno", Collana di Arti, Pensiero e Scienza; Minelli Editore—2006; 54 pgs.
Behl, Marc et al., "Shape-Memory Polymers", Materials Today Apr. 2007; 10(4); 20-28.
Belkas, J. S. et al., "Peripheral nerve regeneration through a synthetic hydrogel nerve tube", Restorative Neurology and Neuroscience 23 (2005) 19-29.
Bellin, 1. et al., "Polymeric triple-shape materials", Proceedings of the National Academy of Sciences of the United States of America Nov. 28, 2006; 2103(48):18043-18047.
Boenisch, U.W. et al 'Pull-Out strength and stiffness of meniscal repair using absorbable arrows or Ti-Cron vertical and horizontal loop sutures' American Journal of Sports Medicine, Sep.-Oct. 1999 vol. 27, Issue 5, pp. 626-631.
Buckley, P.R. 'Actuation of Shape Memory Polymer using Magnetic Fields for Applications in Medical Devices' Master of Science in Mechanical Engineering in Massachusetts Institute of Technology Jun. 2003, 144 pages.
Buncke, Jr., H.J. et al 'The Suture Repair of One-Millimeter Vessels, microvascular surgery' (1966) Report of First Conference; Oct. 6-7 pp. 24-35.
Bunnell, S. 'Gig pull-out suture for tendons' J Bone Joint Surg. Am (1954) vol. 36A, No. 4 pp. 850-851.
CCPR Centro De Cirurgia Plastica e Reabilitacao Up Lifting (Aptos Threads) http://ccpr.com.br/upl-l.htm, Aug. 19, 2002 pp. 1-2.
Dahlin, Lars, "Techniques of Peripheral Nerve Repair", Scandinavian Journal of Surgery 97: 310-316, 2008.
Datillo, Jr., P.P. 'Knotless Bi-directional Barbed Absorbable Surgical Suture' Dissertation submitted to the Graduate Faculty of North Carolina State University Textile Management and Technology Nov. 2002, 75 pages.
Datillo, Jr. P.P. et al 'Medical Textiles: Application of an Absorbable Barbed Bi-Directional Surgical Suture' (2002) The Journal of Textile and Apparel Technology and Management vol. 2, Issue 2, pp. 1-5.
Datillo, Jr., P. et al 'Tissue holding performance of knotless absorbable sutures' Society for Biomaterials 29th Annual Meeting Transactions (2003) p. 101.
Declaration of Dr. Gregory L. Ruff, dated Aug. 19, 2005, 8 pages, with Exhibits A-E.
De Persia, Raúl et al., "Mechanics of Biomaterials: Sutures After the Surgery", Applications of Engineering Mechanics in Medicine, GED-University of Puerto Rico, Mayaguez May 2005, p. F1-F27.
Delorenzi, C.L., "Barbed Sutures: Rationale and Technique", Aesthetic Surg. J. Mar. 2006 26(2): 223-229.
Demyttenaere, Sebastian V. et al., "Barbed Suture for Gastrointestinal Closure: A Randomized Control Trial", Surgical Innovation; vol. 16, No. 3; Sep. 2009; pp. 237-242.
Einarsson, Jon I. et al., "Barbed Suture, now in the toolbox of minimally invasive gyn surgery", OBG Management; vol. 21, No. 9; Sep. 2009; pp. 39-41.
Gross, Alex, "Physician perspective on thread lifts", Dermatology Times Feb. 2006 27(2): 2 pages.
Gross, R.A. et al 'Biodegradable Polymers for the Environment' Science (2002) vol. 297, Issue 5582 pp. 803.
Han, H. et al 'Mating and Piercing Micromechanical Suture for Surface Bonding Applications' (1991) Proceedings of the 1991 Micro Electro Mechanical Systems (MEMS>91), An Investigation of Micro Structures, Sensors, Actuators, Machines and Robots pp. 253-258.
Ingle, N.P. et al 'Barbed Suture Anchoring Strength: Applicability to Dissimilar Polymeric Materials' College of Textiles, North Carolina State University, 7th World Biomaterials Congress 2004, 1 page.
Ingle, N.P. et al 'Mechanical Performance and Finite Element Analysis of Bi-directional Barbed Sutures' Master of Science in Textile Technology & Management at North Carolina State University Aug. 2003, 126 pages.
Ingle, N.P. et al., "Optimizing the tissue anchoring performance of barbed sutures in skin and tendon tissues", Journal of Biomechanics 43 (2010); pp. 302-309.
Ingle, Nilesh P et al., "Testing the Tissue-holding Capacity of Barbed Sutures", College of Textiles, North Carolina State University, Fiber Science, the Next Generation Oct. 17-19, 2005, New Jersey Tnstitute of Technology, Newark, NJ, 4 pages.
Jennings et al 'A New Technique in primary tendon repair' Surg. Gynecol. Obstet. (1952) vol. 95, No. 5 pp. 597-600.
Jeong, H.E. et al 'A nontransferring dry adhesive with hierarchial polymer nanohairs' PNAS 106 (14) pp. 5639-5644 (2009).
Kaminer, M. et al., "ContourLift™: A New Method of Minimally Invasive Facial Rejuvenation", Cosmetic Dermatology Jan. 2007; 20(1): 29-35.
Kelch et al., "Shape-memory Polymer Networks from Olio[(∈-hydroxycaproate)-co-glycolate]dimethacrylates and Butyl Acrylate with Adjustable Hydrolytic Degradation Rate", Biomacromolecules 2007;8(3):1018-1027.
Khademhosseini, Ali et al., "Nanobiotechnology Drug Delivery and Tissue Engineering", Chemical Engineering Progress 102:38-42 (2006).
Kuniholm J.F. et al 'Automated Knot Tying for Fixation in Minimally Invasive, Robot Assisted Cardiac Surgery' Master of Science in Mechanical & Aerospace Engineering at North Carolina State University May 2003, 71 pages.
Lendlein, A. et al 'Biodegradable, Elastic Shape-Memory Polymers for Potential Biomedical Applications' (2002) Science vol. 296 pp. 1673-1676.
Lendlein, A. et al 'Shape-Memory Polymers' Agnew Chem. Int. Ed. (2002) vol. 41 pp. 2034-2057.
Leung, J. et al 'Barbed, Bi-directional Medical Sutures: Biomechanical Properties and Wound Closure Efficacy Study' 2002 Society for Biomaterials 28th Annual Meeting Transactions 1 page.
Leung, J. et al 'Barbed, Bi-directional Surgical Sutures' International Conference & Exhibition on Healthcare & Medical Textiles, Jul. 8-9, 2003 pp. 1-8.
Leung, J. et al 'Barbed, Bi-directional Surgical Sutures: In Vivo Strength and Histopathology Evaluations' 2003 Society for Biomaterials 29th Annual Meeting Transactions pp. 100.

(56) References Cited

OTHER PUBLICATIONS

Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.

Leung, J. et al 'Performance Enhancement of a Knotless Suture via Barb Geometry Modifications' 7th World Biomaterials Congress 2004, 1 page.

Li, Y.Y. et al 'Polymer Replicas of Photonic Porous Silicon for Sensing and Drug Delivery Applications' (2003) Science vol. 299 pp. 2045-2047.

Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.

Madduri, Srinivas, et al., "Neurotrophic factors release from nerve conduits for peripheral axonal regeneration", European Cells and Materials vol. 16; Suppl. 1 (2008), p. 14.

Madhave et al 'A biodegradable and biocompatible gecko-inspired tissue adhesive' PNAS 105(7) pp. 2307-2312 (2008).

Maitland et al., "Prototype laser-activated shape memory polymer foam device for embolic treatment of aneurysms", Journal of Biomedical Optics May/Jun. 2007;12(3): pp. 030504-1 to 030504-3.

Malina, M. et al 'Endovascular AAA Exclusion: Will Stents with Hooks and Barbs Prevent Stent-Graft Migration' Journal Endovascular Surgery (1998) vol. 5 pp. 310-317.

Mansberger et al 'A New Type Pull-Out Wire for Tendon Surgery: A Preliminary Report' Department of Surgery, University Hospital and University of Maryland School of Medicine, Baltimore, Maryland, Received for Publication May 10, 1951 pp. 119-121.

Martin, D.P. et al 'Medical applications of poly-4-hydroxybutyrate: a strong flexible absorbable biomaterial' Biochemical Engineering Journal vol. 16 (2003) pp. 97-105.

Mason, M.L. 'Primary and Secondary Tendon Suture. A discussion of the significance of technique in tendon surgery' (1940) Surg Gynecol Obstet 70.

McKee, GK 'Metal anastomosis tubes in tendon suture' The Lancet (1945) pp. 659-660.

McKenzie 'An Experimental Multiple Barbed Suture for the Long Flexor Tendons of the Palm and Fingers' The Journal of Bone and Joint Surgery (1967) vol. 49B, No. 3 pp. 440-447.

Middleton and Tipton 'Synthetic Biodegradable Polymers as Medical Devices' (1998) Medical Plastics and Biomaterials Magazine, 9 pages.

Moran et al., "Bidirectional-Barbed Sutured Knotless Running Anastomosis v Classic van Velthovan in a Model System", Journal of Endourology Oct. 2007; 21(10); 1175-1177.

Mullner, "Metal Foam Has a Good Memory", Dec. 18, 2007 Original story at <http://www.physorg.com/news117214996.html>.

Murtha et al., "Evaluation of a Novel Technique for Wound Closure Using a Barbed Suture", Journal of the American Society of Plastic Surgeons 2006; 117(6); 1769-1780.

Nie, Zhihong and Kumacheva, Eugenia, "Patterning surfaces with functional polymers", Nature Materials vol. 7(2008): 277-290.

Paul, Malcolm D., "Bidirectional Barbed Sutures for Wound Closure: Evolution and Applications", Journal of the American College of Certified Wound Specialists (2009) 1, 51-57.

Paul, Malcolm D. and Rui Avelar, "Quill™ SRS Techniques & Procedures a Novel Approach to Soft Tissue Approximation", Canada, Angiotech Pharmaceuticals, Inc., First Edition Aug. 2007: 20 pages.

Paul, Malcolm D. and Rui Avelar, "Quill™ SRS Techniques & Procedures a Novel Approach to Soft Tissue Approximation", Canada, Angiotech Pharmaceuticals, Inc., Second Edition Aug. 2008: 20 pages.

Paul, Malcolm D. and Rui Avelar, "Quill™ SRS Techniques & Procedures a Novel Approach to Soft Tissue Approximation", Canada, Angiotech Pharmaceuticals, Inc., Third Edition 2009, 8 2007-2009: 27 pages.

Paul, Malcolm D. and Rui Avelar, "Quill™ SRS Techniques & Procedures a Novel Approach to Soft Tissue Approximation", Canada, Angiotech Pharmaceuticals, Inc., Fourth Edition 2010, 8 2007-2010: 27 pages.

Paul, Malcolm D., "Using Barbed Sutures in Open/Subperiosteal Midface Lifting", Aesthetic Surgery Journal 2006(26): 725-732.

Potenza, A. 'Tendon Healing Within the Flexor Digital Sheath in the Dog: An Experimental Study' Journal of Bone & Joint Surgery (1962) vol. 44A No. 1 pp. 49-64.

Pulvertaft 'Suture Materials and Tendon Junctures' American Journal of Surgery (1965) vol. 109 pp. 346-352.

Quill Medical, Inc. 'Barbed Sutures, wrinkle filters give patients more innovative, non-surgical options' Press Release of Program presented at American Society of Plastic Surgeons annual scientific meeting; Philadelphia, Oct. 9, 2004 3 pages.

Quill Medical, Inc. 'Quill Medical's Novel-Self-Anchoring Surgical Suture Approved for Sale in Europe' Press Release; Research Triangle Park, N.C. May 10, 2004, 1 page.

Quill Medical, Inc., "Quill Medical, Inc. Receives FDA Clearance for First-in-Class Knot-Less Self-Anchoring Surgical Suture", Press Release; Research Triangle Park, N.C., Nov. 4, 2004, 1 page.

Richert, Ludovic, et al., "Surface Nanopatterning to Control Cell Growth", Advanced Materials 2008(15): 1-5.

Rodeheaver, G.T. et al., "Barbed Sutures for Wound Closure: In Vivo Wound Security, Tissue Compatibility and Cosmesis Measurements", Society for Biomaterials 30th Annual Meeting Transactions, 2005, 2 pages.

Rofin-Baasel 'Laser Marking on Plastic Materials' (2001) RB50.0, Rofin-Baasel Inc. 2 pages.

Ruff, Gregory, "Technique and Uses for Absorbable Barbed Sutures", Aesthetic Surgery Journal Sep./Oct. 2006; 26:620-628.

Scherman, Peter et al., "Sutures as longitudinal guides for the repair of nerve defects—Influence of suture numbers and reconstruction of nerve bifurcations", Restorative Neurology and Neuroscience 23 (2005) 79-85.

Schmid A. et al 'The outspreading anchor cord. A material for arthroscopic suturing of a fresh anterior cruciate ligament rupture Surgical Clinic of the University of Gottingen' (1987) pp. 417-426.

Semenov, G.M. et al 'Surgical Suture' (2001) Peter, Saint Petersburg, pp. 12-13 and 92-98.

Serafetinides, AA 'Short pulse laser beam interactions with polymers biocompatible materials and tissue' Proce SPIE vol. 3052 (1996) pp. 111-123.

Sulamanidze, M. et al., "APTOS Suture Lifting Methods: 10 Years of Experience", Clin Plastic Surg 36 (2009); pp. 281-306.

Sulamanidze, M.A. et al 'Clinical aspects of bloodless facelift using APTOS filaments' A.V. Vishnevsky Institute of Surgery, Bol'shaya Serpukhovskaya ul, 7, 113811, Moscow, Russia (2002) pp. 24-34.

Sulamanidze, M.A. et al 'Facial lifting with Aptos threads International Journal of Cosmetic Surgery and Aesthetic Dermatology' (2001) No. 4 pp. 1-8.

Sulamanidze, M.A. et al 'Management of Facial Rhytids by Subcutaneous Soft Tissue Dissection' (2000) International Journal of Cosmetic Surgery and Aesthetic Dermatology vol. 2 No. 4 pp. 255-259.

Sulamanidze, M.A. et al 'Morphological foundations of facelift using APTOS filaments' Bolshaya Serpukhovskaya ul 27, 113811 Moscow, Russia (2002) pp. 19-26.

Sulamanidze, M.A. et al 'Removal of Facial Soft Tissue Ptosis with Special Threads' Dermatol Surg (2002) vol. 28 pp. 367-371.

Sulamanidze, MD, M.A., et al., "Soft tissue lifting in the mid-face: old philosophy, new approach-internal stitching technique (Aptos Needle)", Plastic and Aesthetic Surgery Clinic Total Sharm, Moscow, Russia, (2005):15-29.

Sulzle, Inc. B.G. et al Drilled End Surgical Needles Jul. 2002 Syracuse, New York.

Surgical Specialties Corporation, "Wound Closure Catalog"; Summer 2005, 5 pages.

Szarmach, R. et al 'An Expanded Surgical Suture and Needle Evaluation and Selection Program by a Healthcare Resource Management Group Purchasing Organization' Journal of Long-Term Effects of Medical Implants (2003) vol. 13 No. 3 pp. 155-170.

Verdan, C. 'Primary Repair of Flexor Tendons' Journal of Bone and Joint Surgery (1960) vol. 42, No. 4 pp. 647-657.

(56) References Cited

OTHER PUBLICATIONS

Villa, Mark T. et al., "Barbed Sutures: A Review of Literature", Plastic and Reconstructive Surgery; Mar. 2008; vol. 121, No. 3; pp. 102e-108e.
Wu. W. 'Barbed Sutures in Facial Rejuvenation' Aesthetic Surgery Journal (2004) vol. 24 pp. 582-587.
Zoltan, J. 'Cicatrix Optimia: Techniques for Ideal Wound Healing' English language edition University Park Press Baltimore (1977) Chapter 3 pp. 54-55.
US 8,663,276, 03/2014, Leung et al. (withdrawn).
Communication from EPO re: 10000486 dated Apr. 4, 2011, 4 pages.
European Search Report re: EP05025816 dated Jun. 23, 2006.
European Search Report for EP07006258.3 dated May 4, 2007, 4 pages.
European Search Report for EP07015905.8 dated Oct. 2, 2007, 2 pages.
European Search Report for EP07015906 dated Oct. 2, 2007.
European Search Report for EP07016222 dated Jan. 7, 2008.
European Search Report for EP09014651 dated Jan. 12, 2010.
European Search Report for EP10000629.5 dated Mar. 10, 2010, 4 pages.
European Search Report re: EP10000486 dated Apr. 23, 2010.
European Search Report re: 10004453 dated Jun. 15, 2010.
European Search Report for EP10011868.6 dated Dec. 6, 2010, 2 pages.
European Search Report for EP10011869 dated Jan. 20, 2011.
European Search Report for EP10011871.0 dated Dec. 3, 2010, 2 pages.
European Search Report for EP10011872 dated Apr. 20, 2011.
European Search Report for EP10012437 dated Apr. 28, 2011.
European Search Report for EP10186592.1 dated Jan. 19, 2011, 2 pages.
European Search Report for EP10184766 dated Apr. 20, 2011.
Extended European Search Report re: 07015905.8 dated Oct. 23, 2007.
Extended European Search Report re: 07016222.7 dated Jan. 30, 2008.
International Preliminary Examination Report re: PCT/US1998/10478 dated Dec. 11, 1999.
International Preliminary Report re: PCT/US2007/002688 dated Aug. 14, 2008.
International Preliminary Report re: PCT/US2008/060127 dated Oct. 13, 2009.
International Preliminary Report on Patentability re: PCT/US2008/064921 dated Dec. 1, 2009.
International Preliminary Report on Patentability re: PCT/US2008/0075849 dated Mar. 16, 2010.
International Preliminary Report re: PCT/US2008/087788 dated Jun. 22, 2010.
International Preliminary Report re: PCT/US2009/032693 dated Aug. 3, 2010.
International Preliminary Report re: PCT/US2009/034703 dated Aug. 24, 2010.
International Preliminary Report re: PCT/US2009/040545 dated Oct. 19, 2010.
International Preliminary Report re: PCT/US2009/041685 dated Oct. 26, 2010.
International Preliminary Report re: PCT/US2011/035431 dated Nov. 6, 2012.
International Preliminary Report on Patentability re: PCT/US2011/040014 dated Dec. 14, 2012.
International Preliminary Report re: PCT/US2011/059238 dated May 7, 2013.
International Search Report for PCT/US1994/09631 dated Dec. 9, 1994.
International Search Report for PCT/US1998/10478 dated Sep. 23, 1998.
International Search Report for PCT/US2002/027525 dated Dec. 9, 2002, 3 pages.
International Search Report for PCT/US2003/030664 dated May 25, 2004.
International Search Report for PCT/2003/030666 dated Dec. 15, 2004.
International Search Report for PCT/US2003/025088 dated Dec. 29, 2003.
International Search Report re: PCT/US2003/030674 dated Sep. 2, 2004.
International Search Report re: PCT/US2004/014962 dated Feb. 24, 2005.
International Search Report for PCT/US2007/002688 dated Oct. 22, 2007.
International Search Report for PCT/US2007/074658 dated Jun. 12, 2007, 3 pages.
International Search Report for PCT/US2008/060127 dated Sep. 23, 2008, 5 pages.
International Search Report for PCT/US2008/077813 dated Mar. 31, 2009.
International Search Report for PCT/US2008/082009 dated Feb. 16, 2010.
International Search Report for PCT/US2009/032693 dated Aug. 26, 2009.
International Search Report for PCT/US2009/034703 dated Sep. 28, 2009.
International Search Report for PCT/US2009/040545 dated Oct. 29, 2009.
International Search Report for PCT/US2009/041685 dated Dec. 22, 2009.
International Search Report for PCT/US2010/056898 dated Aug. 2, 2011.
International Search Report for PCT/US2010/060889 dated Oct. 11, 2011.
International Search Report for PCT/US2011/034660 dated Feb. 8, 2012.
International Search Report for PCT/US2011/035270 dated Jan. 12, 2012.
International Search Report for PCT/US2011/035271 dated Jan. 12, 2012.
International Search Report re: PCT/L7S2011/035431 dated Jan. 12, 2012.
International Search Report for PCT/US2011/059238 dated May 21, 2012.
Partial European Search Report re: EP05025816 dated Mar. 20, 2006.
Singapore Search Report for Singapore Patent Application No. 200702625-5 dated Nov. 26, 2008, 7 pages.
Singapore Search Report for Singapore Patent Application No. 200702350-0 dated Nov. 26, 2008, 6 pages.
Singapore Search Report for Singapore Patent Application No. 200703688-2 dated Nov. 26, 2008, 7 pages.
Supplementary European Search Report re: EP98923664 dated Jun. 12, 2001.
Supplementary European Search Report re: EP03752630 dated Nov. 17, 2005.
Supplementary European Search Report re: 03770556 dated Nov. 17, 2005.
Supplementary European Search Report re: 03754965 dated Nov. 18, 2005.
Supplementary European Search Report re: EP03785177 dated May 19, 2009.
Supplementary European Search Report re: 07017663 dated Nov. 7, 2007.

\* cited by examiner

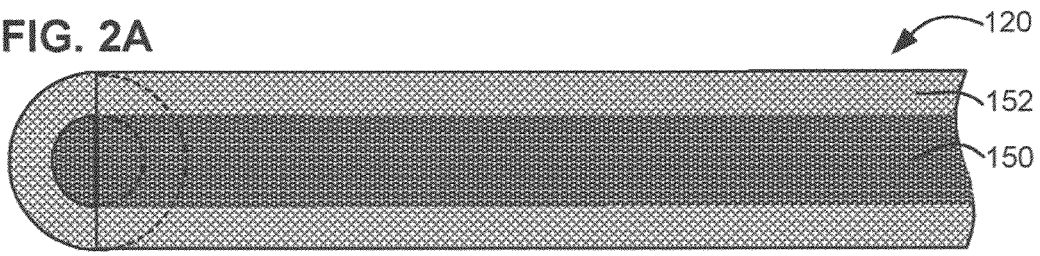
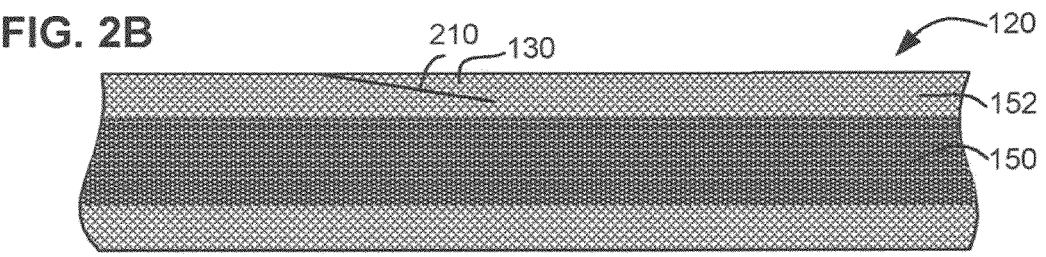
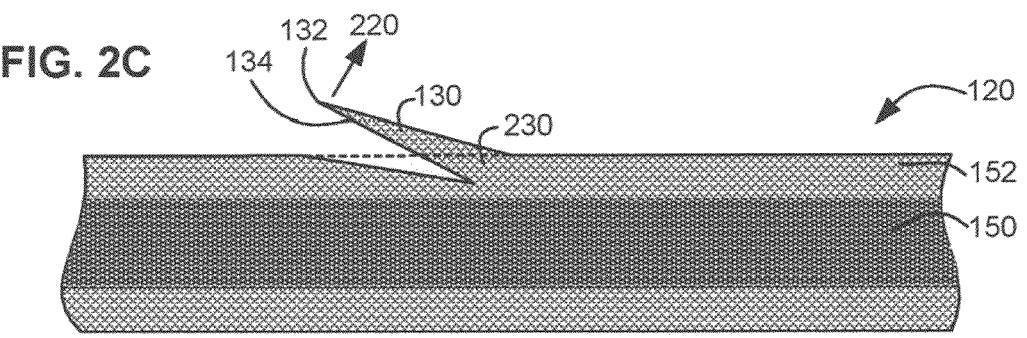
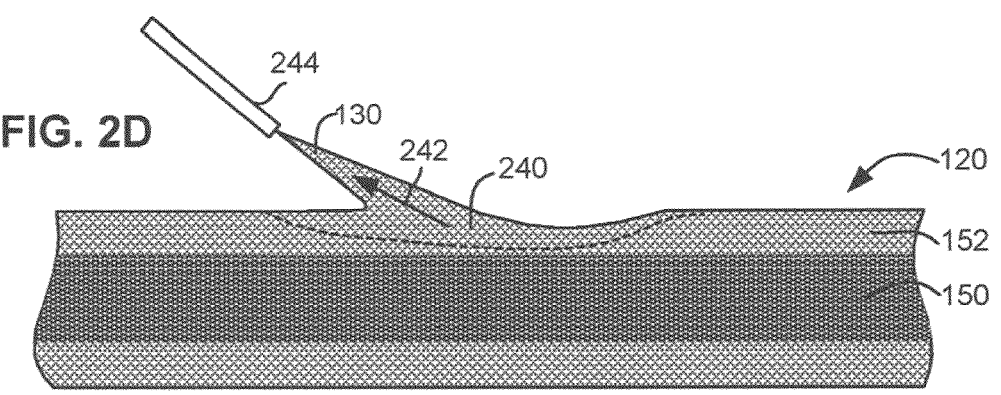

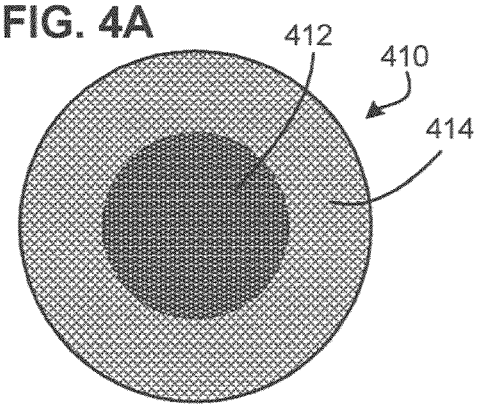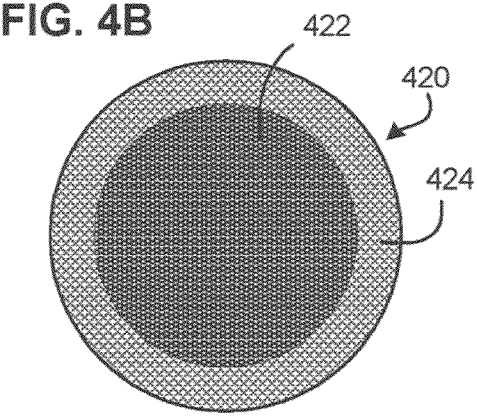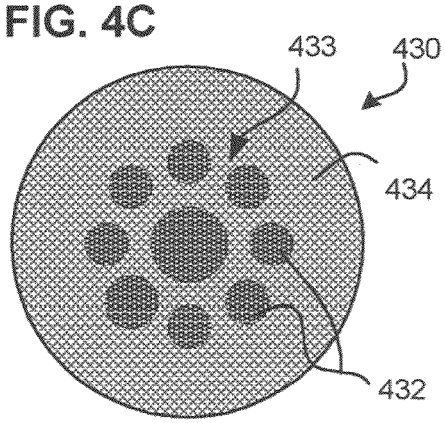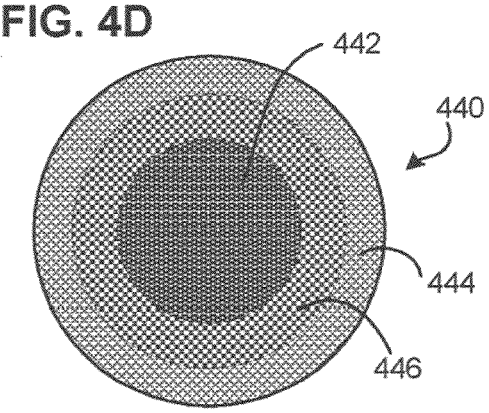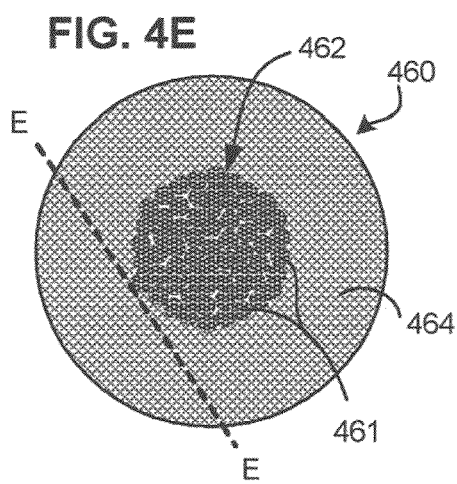

COMPOSITE SELF-RETAINING SUTURES AND METHOD

CROSS-REFERENCE TO RELATED APPLICATIONS

This application is a continuation of U.S. patent application Ser. No. 12/340,530, filed Dec. 19, 2008, which application claims the benefit under 35 U.S.C. §119(e) of U.S. Provisional Patent Application No. 61/015,489 filed Dec. 20, 2007, both of which applications are incorporated herein by reference in their entireties.

FIELD OF INVENTION

The present invention relates generally to self-retaining systems for surgical procedures, methods of manufacturing self-retaining systems for surgical procedures, and uses thereof.

BACKGROUND OF INVENTION

Wound closure devices such as sutures, staples and tacks have been widely used in superficial and deep surgical procedures in humans and animals for closing wounds, repairing traumatic injuries or defects, joining tissues together (bringing severed tissues into approximation, closing an anatomical space, affixing single or multiple tissue layers together, creating an anastomosis between two hollow/luminal structures, adjoining tissues, attaching or reattaching tissues to their proper anatomical location), attaching foreign elements to tissues (affixing medical implants, devices, prostheses and other functional or supportive devices), and for repositioning tissues to new anatomical locations (repairs, tissue elevations, tissue grafting and related procedures) to name but a few examples.

Sutures are often used as wound closure devices. Sutures typically consist of a filamentous suture thread attached to a needle with a sharp point. Suture threads can be made from a wide variety of materials including bioabsorbable (i.e., that break down completely in the body over time), or non-absorbable (permanent; non-degradable) materials. Absorbable sutures have been found to be particularly useful in situations where suture removal might jeopardize the repair or where the natural healing process renders the support provided by the suture material unnecessary after wound healing has been completed; as in, for example, completing an uncomplicated skin closure. Non-degradable (non-absorbable) sutures are used in wounds where healing may be expected to be protracted or where the suture material is needed to provide physical support to the wound for long periods of time; as in, for example, deep tissue repairs, high tension wounds, many orthopedic repairs and some types of surgical anastomosis. Also, a wide variety of surgical needles are available, and the shape, and size of the needle body and the configuration of the needle tip is typically selected based upon the needs of the particular application.

To use an ordinary suture, the suture needle is advanced through the desired tissue on one side of the wound and then through the adjacent side of the wound. The suture is then formed into a "loop" which is completed by tying a knot in the suture to hold the wound closed. Knot tying takes time and causes a range of complications, including, but not limited to (i) spitting (a condition where the suture, usually a knot) pushes through the skin after a subcutaneous closure), (ii) infection (bacteria are often able to attach and grow in the spaces created by a knot), (iii) bulk/mass (a significant amount of suture material left in a wound is the portion that comprises the knot), (iv) slippage (knots can slip or come untied), and (v) irritation (knots serve as a bulk "foreign body" in a wound). Suture loops associated with knot tying may lead to ischemia (knots can create tension points that can strangulate tissue and limit blood flow to the region) and increased risk of dehiscence or rupture at the surgical wound. Knot tying is also labor intensive and can comprise a significant percentage of the time spent closing a surgical wound. Additional operative procedure time is not only bad for the patient (complication rates rise with time spent under anesthesia), but it also adds to the overall cost of the operation (many surgical procedures are estimated to cost between $15 and $30 per minute of operating time).

Self-retaining sutures (including barbed sutures) differ from conventional sutures in that self-retaining sutures possess numerous tissue retainers (such as barbs) which anchor the self-retaining suture into the tissue following deployment and resist movement of the suture in a direction opposite to that in which the retainers face, thereby eliminating the need to tie knots to affix adjacent tissues together (a "knotless" closure). Knotless tissue-approximating devices having barbs have been previously described in, for example, U.S. Pat. No. 5,374,268, disclosing armed anchors having barb-like projections, while suture assemblies having barbed lateral members have been described in U.S. Pat. Nos. 5,584,859 and 6,264,675. Sutures having a plurality of barbs positioned along a greater portion of the suture are described in U.S. Pat. No. 5,931,855, which discloses a unidirectional barbed suture, and U.S. Pat. No. 6,241,747, which discloses a bidirectional barbed suture. Methods and apparatus for forming barbs on sutures have been described in, for example, U.S. Pat. No. 6,848,152. Self-retaining systems for wound closure also result in better approximation of the wound edges, evenly distribute the tension along the length of the wound (reducing areas of tension that can break or lead to ischemia), decrease the bulk of suture material remaining in the wound (by eliminating knots) and reduce spitting (the extrusion of suture material—typically knots—through the surface of the skin. All of these features are thought to reduce scarring, improve cosmesis, and increase wound strength relative to wound closures using plain sutures or staples. Thus, self-retaining sutures, because such sutures avoid knot tying, allow patients to experience an improved clinical outcome, and also save time and costs associated with extended surgeries and follow-up treatments. It is noted that all patents, patent applications and patent publications identified throughout are incorporated herein by reference in their entirety.

The ability of self-retaining sutures to anchor and hold tissues in place even in the absence of tension applied to the suture by a knot is a feature that also provides superiority over plain sutures. When closing a wound that is under tension, this advantage manifests itself in several ways: (i) self-retaining sutures have a multiplicity of retainers which can dissipate tension along the entire length of the suture (providing hundreds of "anchor" points this produces a superior cosmetic result and lessens the chance that the suture will "slip" or pull through) as opposed to knotted interrupted sutures which concentrate the tension at discrete points; (ii) complicated wound geometries can be closed (circles, arcs, jagged edges) in a uniform manner with more precision and accuracy than can be achieved with interrupted sutures; (iii) self-retaining sutures eliminate the need for a "third hand" which is often required for maintaining tension across the wound during traditional suturing and knot tying (to prevent "slippage" when tension is momentarily released during tying); (iv) self-retaining sutures are superior in procedures where knot tying is technically difficult, such as in deep wounds or laparoscopic/endoscopic procedures; and (v) self-retaining sutures can be used to approximate and hold the wound prior to definitive closure. As a result, self-retaining sutures provide easier handling in anatomically tight or deep places (such as the pelvis, abdomen and thorax) and make it easier to approximate tissues in laparoscopic/endoscopic and minimally invasive procedures; all without having to secure the closure via a knot. Greater accuracy allows self-retaining sutures to be used for more complex closures (such as those with diameter mismatches, larger defects or purse string suturing) than can be accomplished with plain sutures.

A self-retaining suture may be unidirectional, having one or more retainers oriented in one direction along the length of the suture thread; or bidirectional, typically having one or more retainers oriented in one direction along a portion of the thread, followed by one or more retainers oriented in another (often opposite) direction over a different portion of the thread (as described with barbed retainers in U.S. Pat. Nos. 5,931,855 and. 6,241,747). Although any number of sequential or intermittent configurations of retainers are possible, a common form of bidirectional self-retaining suture involves a needle at one end of a suture thread which has barbs having tips projecting "away" from the needle until the transition point (often the midpoint) of the suture is reached; at the transition point the configuration of barbs reverses itself about 180° (such that the barbs are now facing in the opposite direction) along the remaining length of the suture thread before attaching to a second needle at the opposite end (with the result that the barbs on this portion of the suture also have tips projecting "away" from the nearest needle). Projecting "away" from the needle means that the tip of the barb is further away from the needle and the portion of suture comprising the barb may be pulled more easily through tissue in the direction of the needle than in the opposite direction. Put another way, the barbs on both "halves" of a typical bidirectional self-retaining suture have tips that point towards the middle, with a transition segment (lacking barbs) interspersed between them, and with a needle attached to either end.

SUMMARY OF INVENTION

Despite the multitude of advantages of unidirectional and bidirectional self-retaining sutures, there remains a need to improve upon the design of the suture such that a variety of common limitations can be eliminated. Specifically, several problems common to existing self-retaining sutures can be addressed by the embodiments of this invention, including, but not limited to: (i) retainers or barbs that are fragile and break or too flexible and bend back, or do not stand proud due to an insufficient ability of the material to plastically deform and as such do not properly engage when deployed in tissue; (ii) inadequate "hold" provided by the retainers for some surgical procedures; resulting in retainers or barbs do not sufficiently anchor in the surrounding tissue and "pull through;" (iii) insufficient contact between the retainers and the surrounding tissue (often occurring when the thread diameter is too small relative to the diameter of the hole created by a larger needle; this limits the ability of the retainers to contact and "grip" the surrounding tissue); (iv) breakage of the self-retaining suture during tensioning and wound approximation; and (v) rotation and slippage of the retainers after deployment. Furthermore, the creation and or deployment of retainer features of self-retaining sutures may be difficult to achieve.

Thus, it would be desirable to provide improved self-retaining sutures which have enhanced ability to anchor into the surrounding tissue, enhanced tissue holding capabilities, enhanced maximum load, and enhanced clinical performance.

It would further be desirable to provide improved methods for making self-retaining sutures that yield retainers which can be more readily created, elevated and deployed.

In accordance with the foregoing background and the limitations of the prior art, the present invention provides, improved self-retaining sutures which have enhanced ability to anchor into the surrounding tissue, enhanced tissue holding capabilities, enhanced maximum load, and enhanced clinical performance and methods for making such self-retaining sutures.

In accordance with another aspect, the present invention provides methods of making self-retaining sutures utilizing a composite filament comprised of two or more different materials.

In accordance with another aspect, the present invention provides self-retaining sutures comprising a composite filament having two of more different materials in which at least one outer material enhances the creation, elevation and deployment of the retainers of the suture.

In accordance with another aspect, the present invention provides sutures comprising a composite filament of two of more different co-extruded materials in which at least one inner material enhances the tensile strength and/or the flexibility of the suture and potentially does this without compromising the creation, elevation, deployment and engagement of the retainers on the suture.

In accordance with a specific embodiment of the present invention a self-retaining suture is made by co-extruding two materials to form a composite filament having a core made from one material that has high strength and flexibility and a sheath made from a different material selected to enhance formation, positioning and strength of a plurality of retainers. In a specific embodiment the sheath material is more plastically deformable than the core material and the core material has more tensile strength than the sheath material such that the suture has an enhanced combination of retainer features and tensile strength compared to a similar suture formed from a single-material filament.

In accordance with specific embodiments of the present invention a self-retaining suture is made by forming a composite filament having a core made from one material that has high strength and a sheath made from a different material. A plurality of retainers is formed from the material of the sheath in the surface of the filament. In specific embodiments the sheath and therefore retainers are made from a material that has a higher elastic constant (and is thus stiffer) and/or a larger plastic zone (and is thus more permanently deformable) than the material of the core. Also, the core material is more elastic and/or more flexible than the material of which the sheath and retainers are made.

The details of one or more embodiments are set forth in the description below. Other features, objects and advantages will be apparent from the description, the drawings, and the claims. In addition, the disclosures of all patents and patent applications referenced herein are incorporated by reference in their entirety.

BRIEF DESCRIPTION OF THE DRAWINGS

Features of the invention, its nature and various advantages will be apparent from the accompanying drawings and the following detailed description of various embodiments.

FIGS. 2A, 2B and 2C are sectional views illustrating steps in the creation of a retainer of a self-retaining suture comprising two materials in accordance with an embodiment of the present invention.

FIG. 2D is a sectional view of an alternative step in the creation of a retainer of a self-retaining suture comprising two materials in accordance with an embodiment of the present invention.

FIGS. 4A-I illustrate alternative configurations of co-extruded suture stock suitable for creation of a self-retaining suture comprising two materials in accordance with embodiments of the present invention.

DETAILED DESCRIPTION

Definitions

Figure 1A:
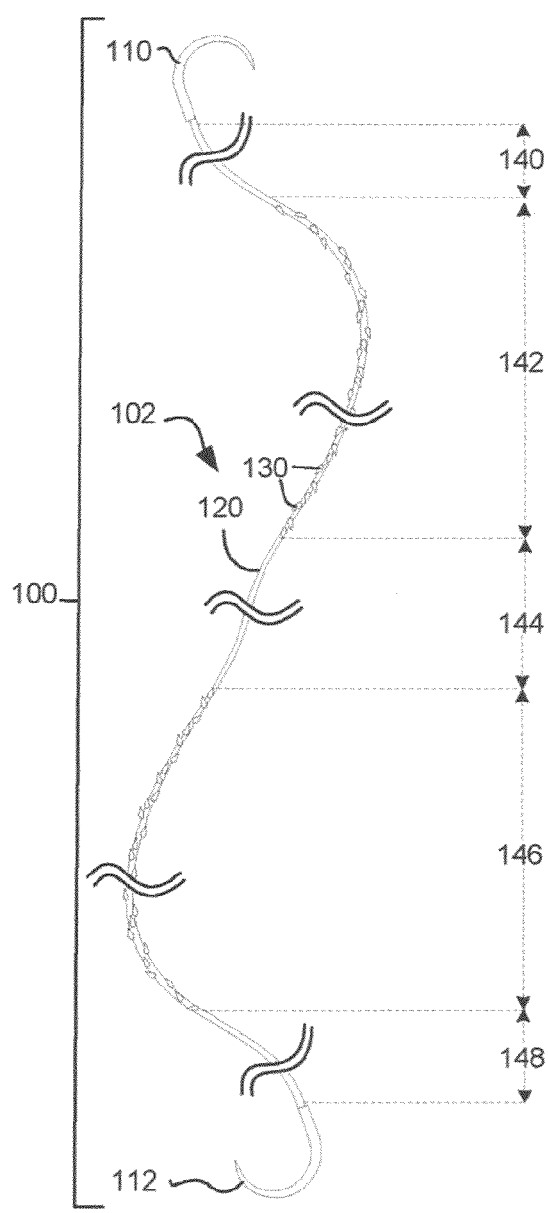
FIGS. 1A and 1B are perspective views of a self-retaining suture comprising two materials in accordance with an embodiment of the present invention.

Definitions of certain terms that may be used hereinafter include the following.

"Self-retaining system" refers to a self-retaining suture together with devices for deploying the suture into tissue. Such deployment devices include, without limitation, suture needles and other deployment devices as well as sufficiently rigid and sharp ends on the suture itself to penetrate tissue.

"Self-retaining suture" refers to a suture that comprises features on the suture filament for engaging tissue without the need for a knot or suture anchor.

"Tissue retainer" (or simply "retainer") or "barb" refers to a physical feature of a suture filament which is adapted to mechanically engage tissue and resist movement of the suture in at least one axial directions. By way of example only, tissue retainer or retainers can include hooks, projections, barbs, darts, extensions, bulges, anchors, protuberances, spurs, bumps, points, cogs, tissue engagers, traction devices, surface roughness, surface irregularities, surface defects, edges, facets and the like. In certain configurations, tissue retainers are adapted to engage tissue to resist movement of the suture in a direction other than the direction in which the suture is deployed into the tissue by the surgeon, by being oriented to substantially face the deployment direction. In some embodiments the retainers lie flat when pulled in the deployment direction and open or "fan out" when pulled in a direction contrary to the deployment direction. As the tissue-penetrating end of each retainer faces away from the deployment direction when moving through tissue during deployment, the tissue retainers should not catch or grab tissue during this phase. Once the self-retaining suture has been deployed, a force exerted in another direction (often substantially opposite to the deployment direction) causes the retainers to be displaced from the deployment position (i.e. resting substantially along the suture body), forces the retainer ends to open (or "fan out") from the suture body in a manner that catches and penetrates into the surrounding tissue, and results in tissue being caught between the retainer and the suture body; thereby "anchoring" or affixing the self-retaining suture in place. In certain other embodiments, the tissue retainers may be configured to permit motion of the suture in one direction and resist movement of the suture in another direction without fanning out or deploying. In certain other configurations, the tissue retainer may be configured or combined with other tissue retainers to resist motion of the suture filament in both directions. Typically a suture having such retainers is deployed through a device such as a cannula which prevents contact between the retainers and the tissue until the suture is in the desired location.

"Retainer configurations" refers to configurations of tissue retainers and can include features such as size, shape, flexibility, surface characteristics, and so forth. These are sometimes also referred to as "barb configurations".

"Bidirectional suture" refers to a self-retaining suture having retainers oriented in one direction at one end and retainers oriented in the other direction at the other end. A bidirectional suture is typically armed with a needle at each end of the suture thread. Many bidirectional sutures have a transition segment located between the two barb orientations.

"Transition segment" refers to a retainer-free (barb-free) portion of a bidirectional suture located between a first set of retainers (barbs) oriented in one direction and a second set of retainers (barbs) oriented in another direction. The transition segment can be at about the midpoint of the self-retaining suture, or closer to one end of the self-retaining suture to form an asymmetrical self-retaining suture system.

"Suture thread" refers to the filamentary body component of the suture. The suture thread may be a monofilament, or comprise multiple filaments as in a braided suture. The suture thread may be made of any suitable biocompatible material, and may be further treated with any suitable biocompatible material, whether to enhance the sutures' strength, resilience, longevity, or other qualities, or to equip the sutures to fulfill additional functions besides joining tissues together, repositioning tissues, or attaching foreign elements to tissues.

"Monofilament suture" refers to a suture comprising a monofilamentary suture thread.

"Braided suture" refers to a suture comprising a multifilamentary suture thread. The filaments in such suture threads are typically braided, twisted, or woven together.

"Degradable suture" (also referred to as "biodegradable suture" or "absorbable suture") refers to a suture which, after introduction into a tissue is broken down and absorbed by the body. Typically, the degradation process is at least partially mediated by, or performed in, a biological system. "Degradation" refers to a chain scission process by which a polymer chain is cleaved into oligomers and monomers. Chain scission may occur through various mechanisms, including, for example, by chemical reaction (e.g., hydrolysis, oxidation/reduction, enzymatic mechanisms or a combination of these) or by a thermal or photolytic process. Polymer degradation may be characterized, for example, using gel permeation chromatography (GPC), which monitors the polymer molecular mass changes during erosion and breakdown. Degradable suture material may include polymers such as polyglycolic acid, copolymers of glycolide and lactide, copolymers of trimethylene carbonate and glycolide with diethylene glycol (e.g., MAXON™, Tyco Healthcare Group), terpolymer composed of glycolide, trimethylene carbonate, and dioxanone (e.g., BIOSYN™ [glycolide (60%), trimethylene carbonate (26%), and dioxanone (14%)], Tyco Healthcare Group), copolymers of glycolide, caprolactone, trimethylene carbonate, and lactide (e.g., CAPROSYN™, Tyco Healthcare Group). A dissolvable suture can also include partially deacetylated polyvinyl alcohol. Polymers suitable for use in degradable sutures can be linear polymers, branched polymers or multi-axial polymers. Examples of multi-axial polymers used in sutures are described in U.S. Patent Application Publication Nos. 20020161168, 20040024169, and 20040116620. Sutures made from degradable suture material lose tensile strength as the material degrades. Degradable sutures can be in either a braided multifilament form or a monofilament form.

"Non-degradable suture" (also referred to as "non-absorbable suture") refers to a suture comprising material that is not degraded by chain scission such as chemical reaction processes (e.g., hydrolysis, oxidation/reduction, enzymatic mechanisms or a combination of these) or by a thermal or photolytic process. Non-degradable suture material includes polyamide (also known as nylon, such as nylon 6 and nylon 6,6), polyester (e.g., polyethylene terephthlate), polytetrafluoroethylene (e.g., expanded polytetrafluoroethylene), polyether-ester such as polybutester (block copolymer of butylene terephthalate and polytetra methylene ether glycol), polyurethane, metal alloys, metal (e.g., stainless steel wire), polypropylene, polyethelene, silk, and cotton. Sutures made of non-degradable suture material are suitable for applications in which the suture is meant to remain permanently or is meant to be physically removed from the body.

"Suture diameter" refers to the diameter of the body of the suture. It is to be understood that a variety of suture lengths may be used with the sutures described herein and that while the term "diameter" is often associated with a circular periphery, it is to be understood herein to indicate a cross-sectional dimension associated with a periphery of any shape. Suture sizing is based upon diameter. United States Pharmacopeia ("USP") designation of suture size runs from 0 to 7 in the larger range and 1-0 to 11-0 in the smaller range; in the smaller range, the higher the value preceding the hyphenated zero, the smaller the suture diameter. The actual diameter of a suture will depend on the suture material, so that, by way of example, a suture of size 5-0 and made of collagen will have a diameter of 0.15 mm, while sutures having the same USP size designation but made of a synthetic absorbable material or a non-absorbable material will each have a diameter of 0.1 mm. The selection of suture size for a particular purpose depends upon factors such as the nature of the tissue to be sutured and the importance of cosmetic concerns; while smaller sutures may be more easily manipulated through tight surgical sites and are associated with less scarring, the tensile strength of a suture manufactured from a given material tends to decrease with decreasing size. It is to be understood that the sutures and methods of manufacturing sutures disclosed herein are suited to a variety of diameters, including without limitation 7, 6, 5, 4, 3, 2, 1, 0, 1-0, 2-0, 3-0, 4-0, 5-0, 6-0, 7-0, 8-0, 9-0, 10-0 and 11-0.

"Suture deployment end" refers to an end of the suture to be deployed into tissue; one or both ends of the suture may be suture deployment ends. The suture deployment end may be attached to a deployment device such as a suture needle, or may be sufficiently sharp and rigid to penetrate tissue on its own.

"Armed suture" refers to a suture having a suture needle on at least one suture deployment end.

"Needle attachment" refers to the attachment of a needle to a suture requiring same for deployment into tissue, and can include methods such as crimping, swaging, using adhesives, and so forth. The suture thread is attached to the suture needle using methods such as crimping, swaging and adhesives. Attachment of sutures and surgical needles is described in U.S. Pat. Nos. 3,981,307, 5,084,063, 5,102,418, 5,123,911, 5,500,991, 5,722,991, 6,012,216, and 6,163,948, and U.S. Patent Application Publication No. US 2004/0088003). The point of attachment of the suture to the needle is known as the swage.

"Suture needle" refers to needles used to deploy sutures into tissue, which come in many different shapes, forms and compositions. There are two main types of needles, traumatic needles and atraumatic needles. Traumatic needles have channels or drilled ends (that is, holes or eyes) and are supplied separate from the suture thread and are threaded on site. Atraumatic needles are eyeless and are attached to the suture at the factory by swaging or other methods whereby the suture material is inserted into a channel at the blunt end of the needle which is then deformed to a final shape to hold the suture and needle together. As such, atraumatic needles do not require extra time on site for threading and the suture end at the needle attachment site is generally smaller than the needle body. In the traumatic needle, the thread comes out of the needle's hole on both sides and often the suture rips the tissues to a certain extent as it passes through. Most modern sutures are swaged atraumatic needles. Atraumatic needles may be permanently swaged to the suture or may be designed to come off the suture with a sharp straight tug. These "pop-offs" are commonly used for interrupted sutures, where each suture is only passed once and then tied. For barbed sutures that are uninterrupted, these atraumatic needles are preferred.

Suture needles may also be classified according to the geometry of the tip or point of the needle. For example, needles may be (i) "tapered" whereby the needle body is round and tapers smoothly to a point; (ii) "cutting" whereby the needle body is triangular and has a sharpened cutting edge on the inside; (iii) "reverse cutting" whereby the cutting edge is on the outside; (iv) "trocar point" or "taper cut" whereby the needle body is round and tapered, but ends in a small triangular cutting point; (v) "blunt" points for sewing friable tissues; (vi) "side cutting" or "spatula points" whereby the needle is flat on top and bottom with a cutting edge along the front to one side (these are typically used for eye surgery).

Suture needles may also be of several shapes including, (i) straight, (ii) half curved or ski, (iii) ¼ circle, (iv) ⅜ circle, (v) ½ circle, (vi) ⅝ circle, (v) and compound curve.

Suturing needles are described, for example, in U.S. Pat. Nos. 6,322,581 and 6,214,030 (Mani, Inc., Japan); and U.S. Pat. No. 5,464,422 (W.L. Gore, Newark, Del.); and U.S. Pat. No. 5,941,899; U.S. Pat. No. 5,425,746; U.S. Pat. No. 5,306,288 and U.S. Pat. No. 5,156,615 (US Surgical Corp., Norwalk, Conn.); and U.S. Pat. No. 5,312,422 (Linvatec Corp., Largo, Fla.); and U.S. Pat. No. 7,063,716 (Tyco Healthcare, North Haven, Conn.). Other suturing needles are described, for example, in U.S. Pat. Nos. 6,129,741; 5,897,572; 5,676, 675; and 5,693,072. The sutures described herein may be deployed with a variety of needle types (including without limitation curved, straight, long, short, micro, and so forth), needle cutting surfaces (including without limitation, cutting, tapered, and so forth), and needle attachment techniques (including without limitation, drilled end, crimped, and so forth). Moreover, the sutures described herein may themselves include sufficiently rigid and sharp ends so as to dispense with the requirement for deployment needles altogether.

"Needle diameter" refers to the diameter of a suture deployment needle at the widest point of that needle. While the term "diameter" is often associated with a circular periphery, it is to be understood herein to indicate a cross-sectional dimension associated with a periphery of any shape.

"Wound closure" refers to a surgical procedure for closing of a wound. An injury, especially one in which the skin or another external or internal surface is cut, torn, pierced, or otherwise broken is known as a wound. A wound commonly occurs when the integrity of any tissue is compromised (e.g., skin breaks or burns, muscle tears, or bone fractures). A wound may be caused by an act, such as a puncture, fall, or surgical procedure; by an infectious disease; or by an underlying medical condition. Surgical wound closure facilitates the biological event of healing by joining, or closely approximating, the edges of those wounds where the tissue has been torn, cut, or otherwise separated. Surgical wound closure directly apposes or approximates the tissue layers, which serves to minimize the volume new tissue formation required to bridge the gap between the two edges of the wound. Closure can serve both functional and aesthetic purposes. These purposes include elimination of dead space by approximating the subcutaneous tissues, minimization of scar formation by careful epidermal alignment, and avoidance of a depressed scar by precise eversion of skin edges.

'Tissue elevation procedure" refers to a surgical procedure for repositioning tissue from a lower elevation to a higher elevation (i.e. moving the tissue in a direction opposite to the direction of gravity). The retaining ligaments of the face support facial soft tissue in the normal anatomic position. However, with age, gravitational effects and loss of tissue volume effect downward migration of tissue, and fat descends into the plane between the superficial and deep facial fascia, thus causing facial tissue to sag. Face-lift procedures are designed to lift these sagging tissues, and are one example of a more general class of medical procedure known as a tissue elevation procedure. More generally, a tissue elevation procedure reverses the appearance change that results from effects of aging and gravity over time, and other temporal effects that cause tissue to sag, such as genetic effects. It should be noted that tissue can also be repositioned without elevation; in some procedures tissues are repositioned laterally (away from the midline), medially (towards the midline) or inferiorly (lowered) in order to restore symmetry (i.e. repositioned such that the left and right sides of the body "match").

"Medical device" or "implant" refers to any object placed in the body for the purpose of restoring physiological function, reducing/alleviating symptoms associated with disease, and/or repairing and/or replacing damaged or diseased organs and tissues. While normally composed of biologically compatible synthetic materials (e.g., medical-grade stainless steel, titanium and other metals or polymers such as polyurethane, silicon, PLA, PLGA and other materials) that are exogenous, some medical devices and implants include materials derived from animals (e.g., "xenografts" such as whole animal organs; animal tissues such as heart valves; naturally occurring or chemically-modified molecules such as collagen, hyaluronic acid, proteins, carbohydrates and others), human donors (e.g., "allografts" such as whole organs; tissues such as bone grafts, skin grafts and others), or from the patients themselves (e.g., "autografts" such as saphenous vein grafts, skin grafts, tendon/ligament/muscle transplants). Medical devices that can be used in procedures in conjunction with the present invention include, but are not restricted to, orthopedic implants (artificial joints, ligaments and tendons; screws, plates, and other implantable hardware), dental implants, intravascular implants (arterial and venous vascular bypass grafts, hemodialysis access grafts; both autologous and synthetic), skin grafts (autologous, synthetic), tubes, drains, implantable tissue bulking agents, pumps, shunts, sealants, surgical meshes (e.g., hernia repair meshes, tissue scaffolds), fistula treatments, spinal implants (e.g., artificial intervertebral discs, spinal fusion devices, etc.) and the like.

Composite Self-Retaining Sutures

As discussed above, the present invention provides compositions, configurations, methods of manufacturing and methods of using self-retaining systems in surgical procedures which greatly increase the ability of the self-retaining sutures to anchor into the surrounding tissue to provide superior holding strength and improve clinical performance. In accordance with one embodiment, the present invention comprises a self-retaining suture comprising a composite filament made from two or more different materials.

A. Self-Retaining Composite Suture System

FIG. 1A illustrates a bidirectional self-retaining composite suture system 100. Self-retaining suture system 100 comprises needles 110, 112 attached to self-retaining composite suture thread 102. Self-retaining composite suture thread 102 includes a plurality of retainers 130 distributed on the surface of a composite filament 120. In lead-in region 140 of composite filament 120 there are no retainers 130. In region 142 of composite filament 120 there are a plurality of retainers 130 arranged such that the suture can be deployed in the direction of needle 110 but resists movement in the direction of needle 112. In transition region 144, there are no retainers 130. In region 146, there are a plurality of retainers 130 arranged such that the suture can be deployed in the direction of needle 112 but resists movement in the direction of needle 110. In lead-in region 148 of composite filament 120 there are no retainers 130. A break is shown in each of regions 140, 142, 144, 146 and 148 to indicate that the length of each region may be varied and selected depending upon the application for which the suture is intended to be used. Although a bidirectional self-retaining suture system 100 is illustrated, the present invention includes self-retaining suture systems of a wide variety of retainer and needle configurations described above. Likewise the configuration of each of needles 110 and 112 can be any of the range of different surgical needles developed for use in different applications. Needles 110 and 112 may have the same configuration or different configurations.

Figure 1B:
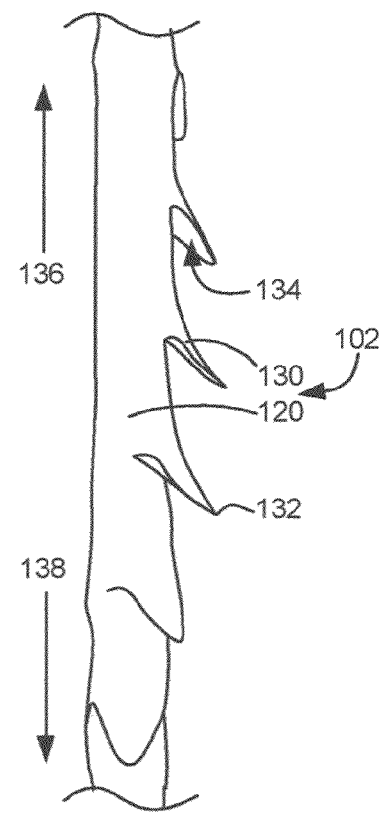

FIG. 1B illustrates a magnified view of self-retaining suture 102 in region 142. As shown in FIG. 1B, a plurality of retainers 130 is distributed on the surface of composite filament 120. The affixation of self-retaining sutures after deployment in tissue entails the penetration of retainer ends into the surrounding tissue resulting in tissue being caught between the retainer and the suture body. The inner surface of the retainer that is in contact with the tissue that is caught between the retainer 130 and the composite filament 120, herein referred to as the "tissue engagement surface" or "inner retainer surface," can be adapted to better engage the tissue. As illustrated in FIG. 1B, each retainer 130 has a tip 132 and tissue retainer surface 134. When self-retaining suture thread 102 is moved in the direction of arrow 136, retainer 130 lies flat against the body of composite filament 120. However, when self-retaining suture thread 102 is moved in the direction of arrow 138, tip 132 or retainer 130 engages tissue surrounding composite filament 120 and causes retainer 130 to fan out from composite filament 120 and engage the tissue with face 134 thereby preventing movement of the suture in that direction.

Figure 1C:
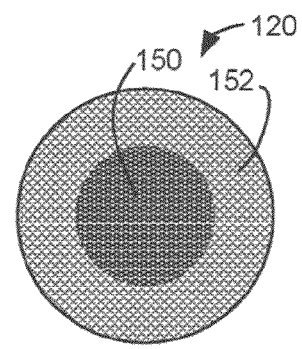
FIG. 1C is a sectional view of the suture of FIGS. 1A and 1B illustrating the arrangement of the two materials.

FIG. 1C shows a cross-sectional view of composite filament 120. As can been seen in FIG. 1C, composite filament 120 includes two materials, a core material 150 and a sheath material 152. Because the retainers 130 are formed on the surface of composite filament 120, the retainers are made, in this embodiment, entirely of sheath material 152. Accordingly, in specific embodiments of the present invention, sheath material 152 is selected to have properties which are advantageous to the creation, elevation, deployment and function of retainers 130. Furthermore, in specific embodiments of the present invention, retainers 130 include little or none of core material 150. Thus, core material 150 is selected to have properties which are advantageous to the mechanical properties of the suture. For example, in certain embodiments sheath material 152 may be selected to have a larger plastic deformation zone (also known as work hardening zone) i.e. more ability to undergo plastic (permanent) deformation than core material 150. This permits retainers 130 to be elevated (bent away) from composite filament 120 and plastically deformed into the elevated position away from composite filament 120. Furthermore, in certain embodiments, core material 150 is selected to have greater tensile strength and/or elasticity, and preferably greater flexibility than sheath material 152 which permits composite filament 120 to have a greater tensile strength and/or resistance to breakage than if the filament was entirely made of the sheath material 152.

In alternative embodiments a retainer 130 may comprise the sheath material 152 and also some portion of the core material 150 or another non-sheath material. In such embodiments the materials are selected such that the composite properties of the materials in the retainer permit or enhance the function of the retainer such as by facilitating elevation of the retainer 130.

B. Retainer Formation and Elevation

Suture threads described herein may be produced by any suitable method, including without limitation, injection molding, stamping, cutting, laser, extrusion, and so forth. With respect to cutting, polymeric thread or filaments may be manufactured or purchased for the suture body, and the retainers can be subsequently cut onto the suture body; the retainers may be hand-cut, laser-cut, or mechanically machine-cut using blades, cutting wheels, grinding wheels, and so forth. During cutting either the cutting device or the suture thread may be moved relative to the other, or both may be moved, to control the size, shape and depth of cut 210. Particular methods for cutting barbs on a filament are described in U.S. patent application Ser. No. 09/943,733 titled "Method Of Forming Barbs On A Suture And Apparatus For Performing Same" to Genova et al., and U.S. patent application Ser. No. 10/065,280 titled "Barbed Sutures" to Leung et al. both of which are incorporated herein by reference.

Referring now to FIGS. 2A, 2B and 2C where an exemplary process for making a retainer 130 in a composite filament 120 is provided. FIG. 2A shows a longitudinal cross-section of filament 120. As shown in FIG. 2A composite filament 120 comprises core material 150 and sheath material 152. Composite filament 120 may be formed by any method known in the art for making a composite filament having two different materials each having the properties required for the function of the material in the filament. One suitable method is co-extrusion of different materials having the required properties as will be further described with respect to FIG. 3A. Another suitable method is extrusion of a material over a preformed filament as will be further described with respect to FIG. 3B. Other methods of forming a coating layer on a preformed filament may also be utilized including, without limitation, dip coating, spray coating, curtain coating and/or chemical deposition (such as chemical vapor deposition CVD).

As shown in FIG. 2B a retainer 130 may be formed on composite filament 120 by making a cut 210 into sheath material 152 of composite filament 120. Cut 210 can be made using any of a wide range of technologies. Such technologies include be hand-cutting, laser-cutting, or mechanically machine-cutting using blades, cutting wheels, grinding wheels, and so forth. Note that in this embodiment, the depth of cut has been selected such that cut 210 is entirely within sheath material 152 and does not penetrate into core material 150. As shown in FIG. 2B, retainer 130 may still lay flat against the surface of composite filament 120 after cut 210 has been made in sheath material 152.

In order for retainer 130 to effectively engage tissue after deployment, tip 132 is preferably elevated above the surface of composite filament 120. As shown in FIG. 2C, after the retainer cutting step of FIG. 2B, retainer 130 is mechanically bent away from the body of composite filament 120 in the direction shown by arrow 220. Tip 132 is moved above the surface of composite filament 120 and tissue engagement surface 134 is exposed. The elevation of retainer 130 can be achieved by a number of mechanisms. In a simple example, a cutting blade is used to form cut 210 and the cutting blade is then removed from cut 210 in a manner that bends retainer 130 away from the body of composite filament 120. In an alternative example, the retainer is mechanically elevated by a device other than the blade.

If sheath material 152 is too elastic, retainer 130 will spring back to the retainer's previous position flush with the surface of composite filament 120 (as shown by the dotted line) after elevation of the retainer. This is also the case if the material does not have the ability to undergo permanent deformation. Thus, in accordance with a specific embodiment of the present invention, sheath material 152 is selected such that it is sufficiently plastically deformable that after retainer 130 has been moved away from composite filament 120, sheath material remains in its new deformed shape with the tip 132 of retainer 130 substantially elevated above the surface of composite filament 120 and tissue engagement surface 134 exposed. Sheath material 152 is selected such that the mechanical movement of tip 132 of retainer away from composite filament 120 is sufficient to plastically deform the region 230 of material 152 at the base of retainer 130 causing it to take on a new permanent shape. However, as such plastic deformation would be undesirable in the suture as a whole, core material 150 is selected to have significantly lower plasticity and significantly higher elasticity and/or tensile strength than sheath material 152.

In other embodiments, retainer 130 may be formed by a process other than cutting into the sheath of the filament. For example, as shown in FIG. 2D retainers can be formed by melting the sheath material 152 in region 240 and then drawing material out of filament 120 with device 244 to form retainer 130 and then cooling the material. In this embodiment the sheath material 152 is selected such that it may be melted and manipulated without disrupting the tensile strength of the core material. In alternative embodiments a preformed retainer may be affixed mechanically, adhesively or by melting to the sheath. The sheath material is in this embodiment selected to enhance the affixation of the retainer to the filament and retention of the retainer by the filament. In another embodiment molten material is formed onto the sheath in the shape of a retainer and the molten material fuses with the sheath material. The sheath material in this case is selected to enhance the adhesion or fusion with the externally applied molten material. In some cases the molten material may be the same material as the sheath.

C. Co-Extrusion of Composite Monofilament

Figure 3A:
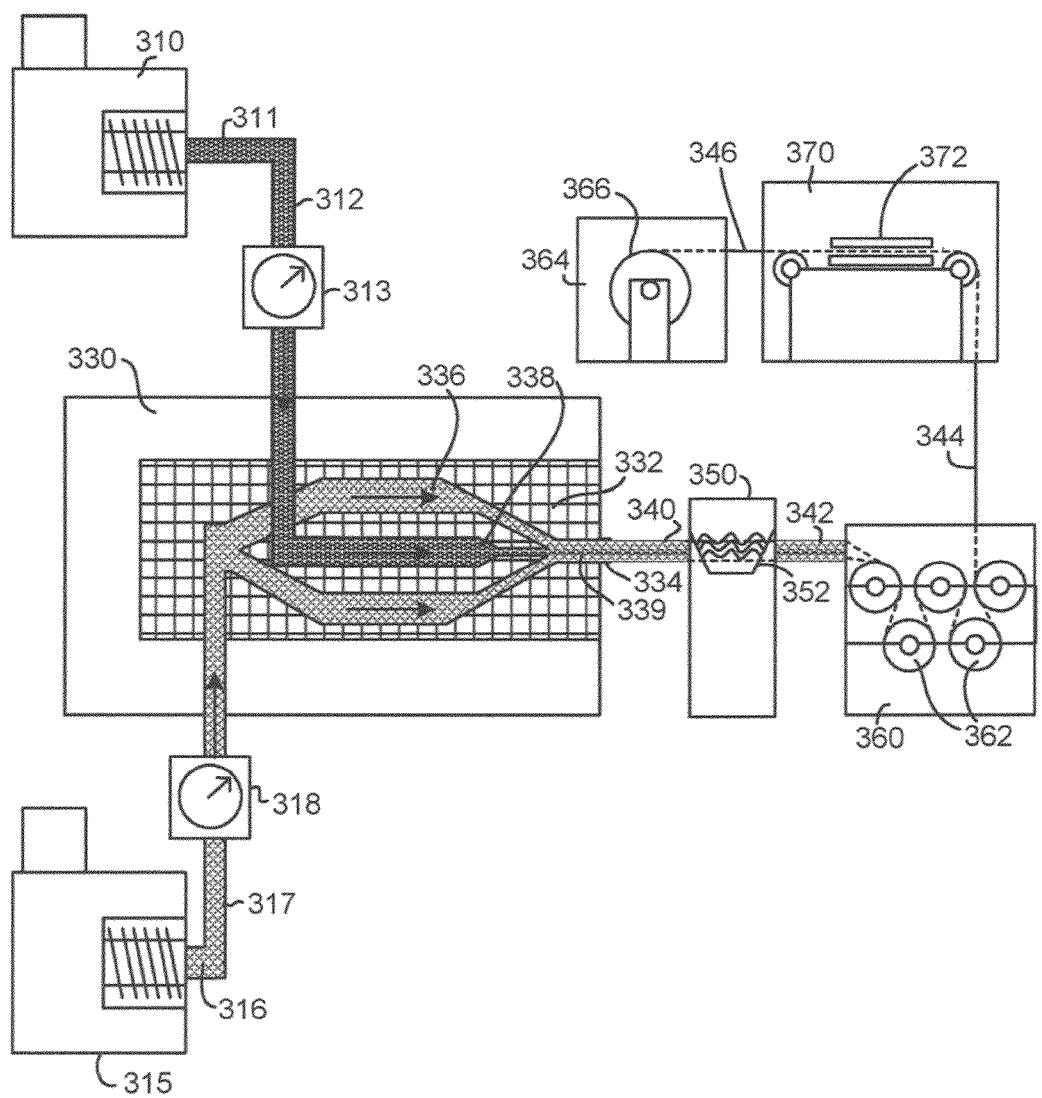
FIG. 3A illustrates a method and apparatus for co-extruding multiple materials to form a composite filament suitable for creation of a self-retaining suture comprising two materials in accordance with an embodiment of the present invention.

As described above, a composite filament can be made in many different ways. In accordance with one embodiment of the invention, a composite monofilament 320 is formed by co-extruding two materials. As shown in FIG. 3A, satellite extruder 310 heats, melts and extrudes a first material 311 along conduit 312 to main extruder 330. Metering pump 313 on conduit 312 controls the flow of first material 311 to main extruder 330. A second satellite extruder 315 heats, melts and extrudes a second material 316 along conduit 317 to main extruder 330. Metering pump 318 on conduit 317 controls the flow of second material 316 to main extruder 330.

In main extruder 330, the two melted materials 311, 316 flow through two flow paths 336, 338 through an extrusion die 332 which controls the arrangement of the two materials 311, 316 when the materials combine in composite flow channel 339. The two materials are combined are combined in composite flow channel 339 as shown and then extruded from die 332 through die exit 334. Die 332 and flow channels 336, 338, 339 are designed and operated such that the two materials 311 and 316 do not mix in composite flow channel 339. The fiber 340 which is still melted material is then solidified by air or liquid cooling in quenching station 350. Quenching station 350 preferably optionally includes a quenching bath 352 for liquid cooling. The solidified filament 342 is then drawn in drawing machine 360. Typically the solidified filament is drawn at temperatures between 30-80% of melting point (Celsius). Usually the suture is extruded then drawn on several rollers with decreasing temperature. Drawing of the filament reduces the diameter of the filament while at the same time orienting the molecules of the polymers of the filament and enhancing the tensile strength of the filament. Typically drawing is conducted in a continuous process by winding the filament around a series of rollers where each roller in the series has a slightly higher roller surface speed. The speed differential of the rollers results in stretching of the filament as the filament passes from roller to roller. The filament may also be tempered by one or more heating and cooling steps before, during or after the drawing process. As illustrated in FIG. 3A, drawn filament 344 is tempered in tempering machine 370 as the filament is passed through heating unit 372. After the filament has been drawn and tempered the finished monofilament 346 is passed to winder 364 where the composite monofilament is wound onto drum 366 until required for preparation of self-retaining sutures.

Figure 3B:
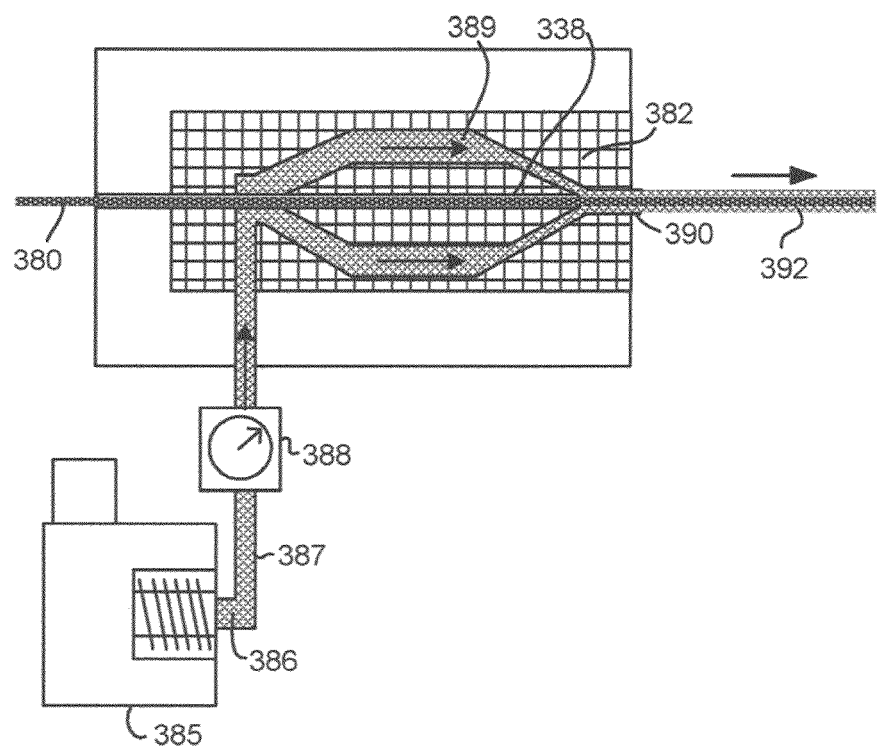
FIG. 3B illustrates a method and apparatus for extruding a material onto a preformed filament to form a composite filament suitable for creation of a self-retaining suture comprising two materials in accordance with an embodiment of the present invention.

FIG. 3B illustrates an alternative method of making a filament suitable for use in embodiments of the present invention. As shown in FIG. 3B, a core filament 380 is drawn through an extrusion die 382. Satellite extruder 385 heats, melts and extrudes a sheath material 386 via conduit 387 to die 382. Metering pump 388 controls the flow of sheath material 386 to flow path 389 of die 382. The rate of supply of sheath material 386 and the rate of movement of core filament 380 are controlled such that a sheath material 386 is evenly coated on the core 380 in the desired cross-section (as determined by the cross-section of the extrusion nozzle 390. A suitable method for making a composite filament comprising a core coated with an extruded material is described in U.S. Pat. No. 6,183,499 titled "Surgical Filament Construction" to Fisher et al. which is incorporated herein by reference. The finished filament 392 comprising core filament 380 and sheath material 386 may be quenched, tempered and drawn and then wound onto a drum as shown in FIG. 3A. However, in certain embodiments, core filament 380 may already have been drawn and no further drawing of finished filament 392 may be necessary or desirable. In some embodiments, for example, a core filament of a core material may be extruded and then drawn. Then the same material may be extruded over the core filament (as shown in FIG. 3B) without subsequent drawing of the filament. The resulting filament has a core and sheath of the same material, however, the sheath material has different physical properties than the core material because the sheath material has not undergone the drawing process.

Although extrusion has been illustrated in FIGS. 3A and 3B, any suitable manufacturing process may be used to form the composite filaments utilized as a stock filament material for embodiments of the present invention. In another preferred embodiment, the composite materials may be spun into fibers to be used as monofilament or multifilament sutures. To produce fibers having the core/sheath structure of FIG. 1, the core and sheath constituent materials are separately melted. The constituent materials are separately fed as polymer melts to a spinneret and are combined in the spinneret just before the spinneret exit orifice. The spinning device may have one or a plurality of spinnerets. The filament produced from a spinneret undergoes subsequent processing such as quenching, drawing and tempering in order to produces a composite filament suitable for use in embodiments of the present invention. Particular apparatus and methods for forming composite monofilaments suitable for use in the present invention can be found in U.S. Pat. No. 7,070,610 titled "Monofilament Suture And Manufacturing Method Thereof" to Im et al. and U.S. Pat. No. 6,315,788 titled "Composite Materials And Surgical Articles Made Therefrom" to Roby both of which are incorporated herein by reference.

D. Filament Configurations

Depending upon the configuration of the extruders, die, spin block, spinneret, or other manufacturing equipment, a composite filament suitable for creating a self-retaining suture in accordance with embodiments of the present invention can be created with a wide variety of different arrangements of different materials. Furthermore, composite filaments can be made using 2, 3, 4 or even more different component materials if necessary or desired for the particular application. Different configurations of composite filaments are useful in specific embodiments of the present invention and are described below with respect to FIGS. 4A-4I.

As shown in FIGS. 4A and 4B simple composite filaments 410, 420 comprise two materials arranged one material in the core and a second material as a sheath over the core. This arrangement of materials in a composite filament can be made by co-extrusion of the two materials. In a simple variation, the two materials may be used in different amounts depending on the use to which the filament will be put. For example in FIG. 4A the core material 412 takes up about 25% of the cross-sectional area of filament 410, with the sheath material 414 taking up 75% of the cross-sectional area. In comparison, in FIG. 4B, the core material 422 and sheath material 424 each take up about 50% of the cross-sectional area. In general, the core material may comprise from 10% to 90% of the total cross-sectional area of the filament. Preferably the core material will comprise from 25% to 90% of the total cross-sectional area of the filament. More preferably the core material will comprise more than 50% of the total cross-sectional area of the filament.

The configuration of the materials in the composite filament will depend upon the characteristics of the materials and the amount of material necessary to fulfill the role of the filament. For example, in one embodiment the material of sheath 414 is chosen to be plastically deformable in order that barbs may be more easily formed and elevated from the surface of the filament. The depth of the sheath may thus be chosen such that the retainers when formed are formed entirely out of the sheath material. Likewise in one embodiment of the present invention the material of the core 412 is chosen because of its characteristic of tensile strength. The strength of the final filament material will depend in large part upon the cross-sectional area of core 412. Thus core 412 is desirably as large as possible while providing sufficient amount of sheath material 414 to permit the formation of retainers. The overall diameter of the suture thread is also limited based upon the surgical needs.

FIG. 4C illustrates an alternative filament 430 in which a plurality of "islands" 432 are present in a surrounding "sea" 434 of the second material. The plurality of islands 432 together comprise a segmented core 433 of filament 430. The "sea" 434 of the second material comprises the sheath and also fills the interstices between the segments 432 of the segmented core 433. This arrangement of materials in a composite filament 430 can be made by co-extrusion of the two materials. The resulting fiber may show a useful combination of the characteristics of the materials. For example, if a unitary core of a first material such as core 412 of FIG. 4A proves to have suitable tensile strength but is too resistant to bending, the configuration of FIG. 4C may, by creating separate regions 432 of the core material separated by more flexible zones 434 of the sheath material be more flexible to bending even if the same cross-sectional area of material (and thus tensile strength) is present. Particular configurations of composite monofilaments can be found in U.S. Pat. No. 7,070,610 titled "Monofilament Suture And Manufacturing Method Thereof" to Im et al. which is incorporated herein by reference.

FIG. 4D illustrates another alternative composite filament 440 for use in the present invention. The composite filament of FIG. 4D is made from three different materials. A first material forms a core 442 of filament 440. A second material 444 forms a sheath on the outer surface of composite filament 442. The third material is sandwiched between the core 440 and the sheath 444 in intermediate layer 446. This arrangement of materials in a composite filament can be made by co-extrusion of the three materials. The material of intermediate layer 446 may be selected, for example, for its mechanical properties as an interface between the core 442 and sheath 444. Alternatively the material of intermediate layer 446 may be selected for favorable interaction with tissues in the retainers as the material of intermediate layer 446 will only be exposed to the tissue where retainers are cut into filament 440. For example, the material of intermediate layer 446 may comprise an adhesive component, a therapeutic component or a material that promotes tissue adherence to the retainer or promotes wound healing as described below.

FIG. 4E illustrates another alternative embodiment in which the core 462 of filament 460 comprises a plurality of filaments 461 braided together. Core 460 is surrounded by a sheath 464. This filament may be prepared by taking a braided thread (such as braided suture) and extruding the sheath onto the braided thread as it is passed through an extrusion die. Note that, as before, sheath 464 is sufficiently thick that creating retainers in the surface of filament 462 does not cut into core 462 or fibers 461 of core 462. For example, the maximum depth of a straight cut for a retainer is illustrated by dashed line E-E. Thus core 462 and the material of its fibers 461 may be engineered for high tensile strength and flexibility while sheath 464 is selected based upon it ability to form, elevate and deploy retainers. A suitable method for making a composite filament comprising a braided core is described in U.S. Pat. No. 6,183,499 titled "Surgical Filament Construction" to Fisher et al. which is incorporated herein by reference.

Figure 4F:
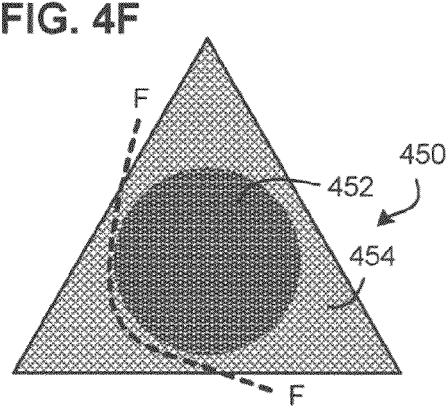

FIG. 4F illustrates an alternative embodiment in which the core and sheaths of filament 450 have different shapes. In the embodiment of FIG. 4F, core 452 has a circular cross-section while the sheath 454 has a triangular cross-section. This arrangement provides a greater volume of the second material at the apices of the triangle while still allowing the core material to provide a high percentage of the total cross-section of the filament. In this embodiment, the retainers are cut into the apices of the triangular cross section thus making optimal use of the material in the sheath 454. In addition, the retainer configuration may be selected such that retainers with arcuate bases are cut into the apices of the triangle. Dashed line F-F illustrates the cut for an arcuate base of a retainer and illustrates that the cut extends through a greater amount of the sheath 454 than would a straight cut. Methods for making self-retaining suture from filaments with triangular or other polyhedral cross-section are disclosed in U.S. Pat. No. 5,342,376 titled "Inserting Device For A Barbed Tissue Connector" to Ruff which is incorporated herein by reference. The arrangement of materials in a composite filament shown in FIG. 4F can be made by co-extrusion of the two materials. The extruder nozzle is selected to have the desired shape. The shape of the cross-section of the filament matches the shape of the extruder nozzle. Alternatively, the filament may be formed as in FIG. 4A and then the sheath material 454 may be formed into the triangular shape by post-extrusion manipulations, such as using rollers to pinch the material into shape and then heating to anneal the polymer into the chosen shape prior to creation of the retainers.

Figure 4G:
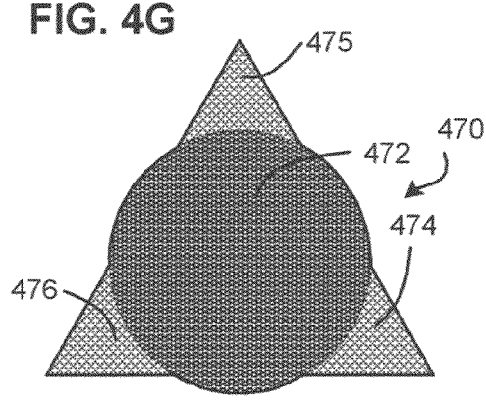
Figure 4H:
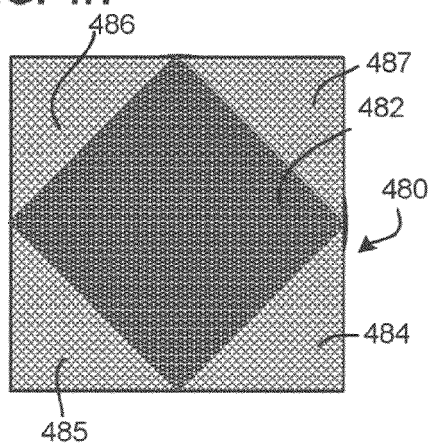
Figure 4I:
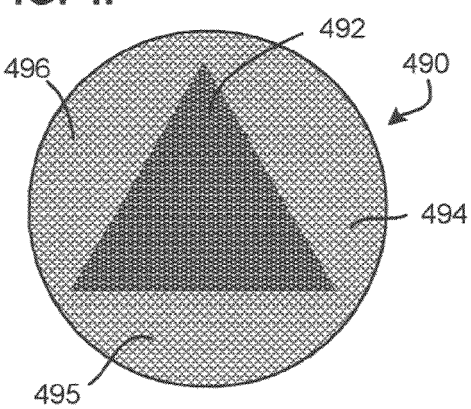

Naturally, other geometric arrangements of the materials are possible, for example the sheath may be formed with a square cross-section, pentagonal, hexagonal or other polygonal cross-section. FIG. 4G illustrates a filament 470 having a sheath comprising three segments 474, 475, 476 over a circular core 472. In this embodiment the sheath is not continuous but comprised of three elements arrayed around core 472. In this embodiment, the retainers are cut into the apices of the sheath elements 474, 475, 476 thus making optimal use of the sheath material for making retainers and providing for a large cross-section of core 472. FIG. 4H illustrates a filament 480 having a square sheath comprising four segments 484, 485, 486, 487 over a square core 482. In this embodiment, the retainers are cut into the apices of the sheath section 484, 485, 486, 487 thus making optimal use of the material in the sheath and providing for a large cross-section of core 482. FIG. 4I illustrates a filament 490 having a circular cross-section wherein the core 492 has a triangular cross-section. In this embodiment, the retainers are preferably cut into the thicker portions of the sheath 494, 495, 496.

E. Filament Materials

It is an advantage of the present invention that the material of the sheath of the filament may have different properties than the material of the core. The material of the sheath may thus be selected to have properties useful for retainer formation, elevation and deployment material and the material of the core may be selected for properties such as strength and flexibility. Suitable materials for the core include many materials that are currently used for making sutures. Suitable non-degradable suture materials for the core material include polyamide (also known as nylon, such as nylon 6 and nylon 6.6), polyester (e.g., polyethylene terephthlate), polytetrafluoroethylenes (e.g., expanded polytetrafluoroethylene), polyether-ester such as polybutester (block copolymer of butylene terephthalate and polytetra methylene ether glycol), 4-hydroxybutyrate, polyhydroxyalkanoate, polyurethane, metals and metal alloys (e.g., stainless steel wire), polypropylene, polyethelene, silk, and cotton. Suitable absorbable materials for the core include polyglycolic acid homopolymer, copolymers of glycolide and ε-caprolactone, copolymers of glycolide and lactide, copolymers of trimethylene carbonate and glycolide with diethylene glycol (e.g., MAXON™, Tyco Healthcare Group), polyhydroxyalkanoates (such as poly(4-hydroxybutyrate) or poly(4-hydroxybutyrate-co-3-hydroxybutyrate)), terpolymer composed of glycolide, trimethylene carbonate, and dioxanone (e.g., BIOSYN™ [glycolide (60%), trimethylene carbonate (26%), and dioxanone (14%)], Tyco Healthcare Group), copolymers of glycolide, caprolactone, trimethylene carbonate, and lactide (e.g., CAPROSYN™, Tyco Healthcare Group).

Suitable core materials are characterized by high yield strength after drawing and sufficient flexibility to ease handling. One suitable core material is copolymer of glycolide and ε-caprolactone, in a ratio of 50/50 to 95/5. More preferably the ratio of glycolide to ε-caprolactone is between preferably 70/30 to 80/20 and most preferably between 72/28 and 78/22. In some embodiments the core material has an elastic constant (Young's modulus) between 60,000 and 600,000 PSI. Preferably the core material has an elastic constant greater than 100,000 PSI. In most embodiments the elastic constant of the core material will be less than 400,000 PSI. However a core material with a higher elastic constant will be suitable if it has sufficient toughness and flexibility. Conversely a material with a lower elastic constant will be suitable if it has a low yield strength and sufficient toughness and a large plastic zone with a sufficiently high ultimate tensile strength (plastic suture can be advantageous in various applications which require permanent deformation to be imposed on the suture during use) or a high yield strength (elastic suture, which can be advantageous in various applications which require compliance). In some embodiments the core material will have a plasticity (amount of plastic deformation as a percentage of total deformation before breaking) of 5-70% and 10-100% elongation at break. However, preferably the core material has a plasticity of around 30% and 15-80% elongation at break. Most suitable core materials will have an elongation at break of 20-50%. The above elastic constant, plasticity and elongation at break values are for the core material as present in the finished suture (after drawing and/or other treatments). Some suitable suture materials may also have more than one elastic constant in the tensile curve which can be represented by two differentially sloped linear regions in the stress-strain curve, in such cases the combination of elastic constants are considered.

Because the retainers are formed from the material or materials of the sheath, the sheath layer or layers may desirably incorporate materials that promote the formation, elevation and deployment of the retainers. Materials that are suitable for the sheath, in some embodiments, are characterized by having a sufficiently small elastic zone and sufficiently large plastic zone to allow for permanent deformation of barbs into an elevated position during cutting and elevation and low recoil after elevating the barbs. It is also desirable to select materials for the sheath with low visco-elastic properties, since in such materials, the recoil may over a time and go undetected immediately after barb cutting and elevation. In certain embodiments the material of the sheath material may be selected to have a larger plastic deformation zone (also known as work hardening zone) i.e. more ability to undergo plastic (permanent) deformation than the material of the core material. This permits retainers formed from the sheath material to be elevated (bent away) from the filament and permanently deformed into the elevated position away from composite filament. For example, suitable materials for the sheath include Nylon 6,6, polydioxanone, polypropylene, non-drawn polycaprolactone, poly(4-hydroxybutyrate), non-drawn polydioxanone. Materials which are not drawn typically exhibit a larger plastic region than those which have been drawn. A disadvantage of non-drawn materials can be low stiffness. It is advantageous in some embodiments to use non-drawn materials in the sheath and increase their crystallinity post barb-making by annealing thereby obtaining a higher stiffness of the barb. The retainers can be treated to increase their stiffness and strength e.g. by appropriate annealing cycles (heating to a certain temperature and cooling at a certain rate) using techniques similar to those taught in U.S. Pat. No. 5,007,922 titled "Method Of Making A Surgical Suture" to Chen et al. which is incorporated herein by reference.

Preferably, the sheath material is also relatively stiff (i.e. the sheath material has a high elastic constant, but a short elastic zone, and a long plastic zone preferably with a large work hardening coefficient) such that the retainers take a large force to plastically deform, but have low recoil and thus remain in the elevated position after deformation. Additionally the sheath material preferably has sufficient flexural strength to prevent barbs from bending backwards during fixation of the suture in the tissues and sufficient strength to prevent barbs from breaking during fixation of the suture in the tissues. In some embodiments the sheath material has a short elastic zone and a high yield strength. Thus, in some embodiments the sheath material has an elongation at onset of yielding (onset of plastic deformation) of less than 10% and more preferably less than 3% elongation. At the same time the sheath preferably has a high work hardening coefficient and large plastic zone. Additionally, the plasticity (amount of plastic deformation as a percentage of total deformation before breaking) of the sheath material is, in some embodiments, higher than the plasticity of the core material. In some embodiments the sheath material has a plasticity which comprises 5-90% of total elongation and an ultimate elongation (elongation at break) of 10-80%. Alternatively the sheath can have a plasticity which comprises 30-80% of the total elongation and an ultimate elongation of 15-60%. Most preferably the plastic zone of the sheath material comprises 60-90% of the ultimate elongation.

The material of the sheath in some embodiments also preferably has a high strain-hardening exponent (also known as work-hardening coefficient). Most materials with a distinctive plastic zone have a strain-hardening exponent of 0.1-0.5. Many materials with a low strain-hardening exponent (tending towards "perfect plastic") are not desirable as a sheath material due to the inability to withstand excess stress post yielding. The sheath material may in some embodiments have a strain-hardening exponent between 0.1 and 0.8 and preferably has a strain-hardening exponent between 0.3 and 0.7. Note that in some embodiments a sheath of non-drawn polymer may be extruded over a core polymer which has already been drawn in which case, the sheath elastic constant, plasticity and elongation at break values reflect the properties of the material without drawing. However, the sheath material may be annealed or otherwise treated after extrusion in order to increase the crystallinity and strength (and therefore stiffness).

It is another advantage of the present invention that the sheath and/or outer layers of the filament may desirably incorporate materials that further promote tissue engagement. In addition to tissue engagement at the retainers, use of tissue engagement-promoting materials in at least part of the suture sheath surface (whether or not such materials also make up all or part of the retainers) can enhance the ability of the sutures to stay in place. One such class of tissue engagement-promoting materials are porous polymers that can be extruded, including both microporous polymers and polymers that can be extruded with bubbles (whether bioabsorbable or nonbioabsorbable). A suture synthesized with such materials in the sheath can have a three-dimensional lattice structure that increases tissue engagement surface area and permits tissue infiltration into the suture body itself, thus having a sheath structure that promotes successful suture use. Moreover, by optimizing pore size, fibroblast ingrowth can be encouraged, further facilitating the suture to be anchored in the tissue. Furthermore, an agent can be utilized in conjunction with the suture (introduced separately or adhered to the suture or incorporated into a material of the suture) to encourage fibrosis. Fibrosis-inducing agents which may be used in conjunction with a self-retaining sutures in accordance with the present invention are described in U.S. Pat. No. 7,166,570 titled "Medical Implants And Fibrosis-Inducing Agents" to Hunter et al. which is incorporated herein by reference.

One such microporous polymer is ePTFE (expanded polytetrafluoroethylene). Self-retaining incorporating ePTFE (and related microporous materials) in the sheath are well-suited to uses requiring a strong and permanent lift (such as breast lifts, face lifts, and other tissue repositioning procedures), as tissue infiltration of the suture results in improved fixation and engraftment of the suture and the surrounding tissue thus providing superior hold and greater longevity of the lift.

Additionally, self-retaining sutures described herein may be provided with therapeutic compositions including, for example, compositions to promote healing and prevent undesirable effects such as scar formation, infection, pain, and so forth. This can be accomplished in a variety of manners, including for example: (a) by directly affixing to the suture a formulation (e.g., by either spraying the suture with a polymer/drug film, or by dipping the suture into a polymer/drug solution), (b) by coating the suture with a substance such as a hydrogel which will in turn absorb the composition, (c) by interweaving formulation-coated thread (or the polymer itself formed into a thread) into the suture structure in the case of multi-filamentary sutures, (d) constructing the suture itself with a composition. Such compositions may include without limitation anti-proliferative agents, anti-angiogenic agents, anti-infective agents, fibrosis-inducing agents, anti-scarring agents, lubricious agents, echogenic agents, anti-inflammatory agents, cell cycle inhibitors, analgesics, and anti-microtubule agents. For example, a composition can be applied to the suture before the retainers are formed, so that when the retainers engage, the engaging surface is substantially free of the coating. In this way, tissue being sutured contacts a coated surface of the suture as the suture is introduced, but when the retainer engages, a non-coated surface of the retainer contacts the tissue. Alternatively, the suture may be coated after or during formation of retainers on the suture if, for example, a fully-coated rather than selectively-coated suture is desired. In yet another alternative, a suture may be selectively coated either during or after formation of retainers by exposing only selected portions of the suture to the coating. The particular purpose to which the suture is to be put or the composition may determine whether a fully-coated or selectively-coated suture is appropriate; for example, with lubricious coatings, it may be desirable to selectively coat the suture, leaving, for instance, the tissue-engaging surfaces of the sutures uncoated in order to prevent the tissue engagement function of those surfaces from being impaired. On the other hand, coatings such as those comprising such compounds as anti-infective agents may suitably be applied to the entire suture, while coatings such as those comprising fibrosing agents may suitably be applied to all or part of the suture (such as the tissue-engaging surfaces). The purpose of the suture may also determine the sort of coating that is applied to the suture; for example, self-retaining sutures having anti-proliferative coatings may be used in closing tumor excision sites, while self-retaining sutures with fibrosing coatings may be used in tissue repositioning procedures and those having anti-scarring coatings may be used for wound closure on the skin. As well, the structure of the suture may influence the choice and extent of coating; for example, sutures having an expanded segment may include a fibrosis-inducing composition on the expanded segment to further secure the segment in position in the tissue. Coatings may also include a plurality of compositions either together or on different portions of the suture, where the multiple compositions can be selected either for different purposes (such as combinations of analgesics, anti-infective and anti-scarring agents) or for the synergistic effects of the combination.

F. Self-Elevating/Self-Deploying Retainers

As described above, in specific embodiments of the present invention retainers are formed in the surface of a composite filament to create a self-retaining suture. Advantageously, a sheath material is plastically deformable such that the retainers may be mechanically elevated after formation and will retain the retainers' elevated position. However, it is also possible, by appropriate selection of filament materials, to create a self-retaining suture in which the retainers elevate without requiring external mechanical intervention or in which the retainers self-elevate to augment the effects of mechanical intervention to produce a greater combined elevation. This is advantageous as it reduces the need for mechanical elevation which is time consuming, expensive and has the potential for weakening the retainers. Depending upon the materials chosen, the retainers can be made to elevate when manufactured or upon insertion into tissue during a procedure.

Figure 5A:
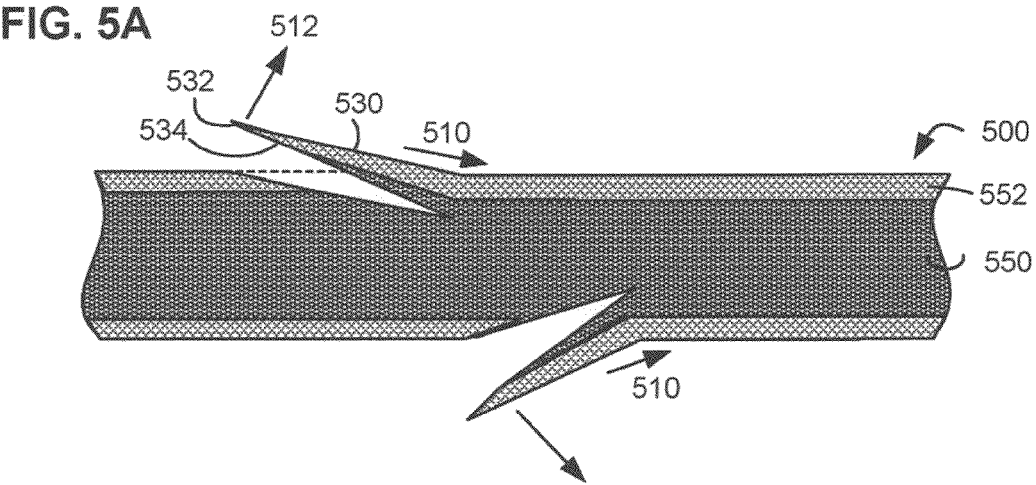
FIGS. 5A-C illustrate particular embodiments of self-retaining sutures comprising a composite filament.

Referring now to FIG. 5A which shows a first example of a self-elevating retainer on a composite filament. In this example, sheath material 552 has been selected such that during the manufacture of filament 500, tension is created in the sheath material 552. This can be achieved, for example by selecting a sheath material that shrinks after the filament has been manufactured while selecting a core material 550 that does not shrink or shrinks less than the sheath material. For example, polyesters such as polyglycolide or polyglycolide copolymers with e-caprolactone, L-lactide will shrink upon heating to about 90-120 C. Thus, a sheath of this material may be selectively shrunk relative to the core prior to forming retainers.

Alternatively a residual stress may be left in the sheath material compared to the core material by the extrusion and drawing process. When a cut is made through the sheath material 552, the tension in sheath material 552 causes the sheath to contract as shown by arrows 510. Contraction of the sheath causes the retainers to elevate from the position shown by the dotted line to the position shown in FIG. 3A in the direction of arrows 512. Thus, in this example, the retainers 530 elevate themselves without mechanical intervention directly upon creating a cut in the surface of the filament 500.

Figure 5B:
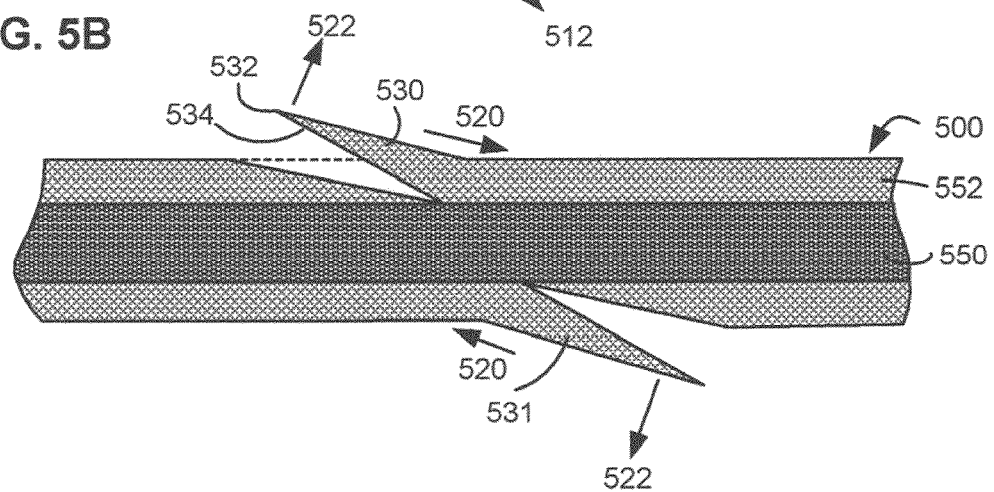

Referring now to FIG. 5B which shows a second example of a self-elevating retainer on a composite filament. In this example, sheath material 552 has been selected such that a tension is created in the sheath material 552 only upon deployment of filament 500, into the tissue of a patient. Thus, the retainers do not elevate until after the self-retaining suture has been positioned in the tissue of the body. This can be achieved, for example by selecting a sheath material that shrinks when exposed to body temperature, moisture, pH or another natural chemical property of tissue to which the sheath material will only be exposed when deployed in the body. For example, polyether-ester shape memory polymers can be activated to undergo contraction at transition temperatures near body temperature. Core material 550 is selected that does not shrink or shrinks less than the sheath material and is also selected to enhance the mechanical strength of the suture. Thus, when the suture is deployed into tissues of the body, sheath 552 contracts in the direction of arrows 520, and core 550 does not contract. Contraction of the sheath causes the retainers 530 to elevate from the position shown by the dotted line to the position shown in FIG. 5B in the direction of arrows 522. Thus, in this example, the retainers 530 elevate themselves without mechanical intervention after introducing the suture into the tissues of a patient. This has the advantage that the suture can be inserted into the tissue in either direction prior to elevation of the retainers. Furthermore, as shown in FIG. 5B, retainers 530 and 531 face in opposite directions and may be included in the same segment of suture. Only after positioning in the tissues of the body do the retainers elevate and prevent movement of the filament in both directions.

In alternative embodiments, an external stimulus may be required to cause elevation of the retainers. Such an external stimulus may be, for example, the application of heat to cause a temperature rise in the suture in excess of natural body temperature. The temperature rise can be caused by heating the suture outside the body prior to deployment. Alternatively, magnetic particles may be embedded in the material of the suture and caused to heat the suture material by magnetic induction caused by application of a magnetic filed through the tissue of the subject after deployment of the suture. Additionally, shape memory polymers which contract upon application of UV light, pH or other stimuli which may be applied to the suture after deployment in the tissues may be used in sheath 552.

Figure 5C:
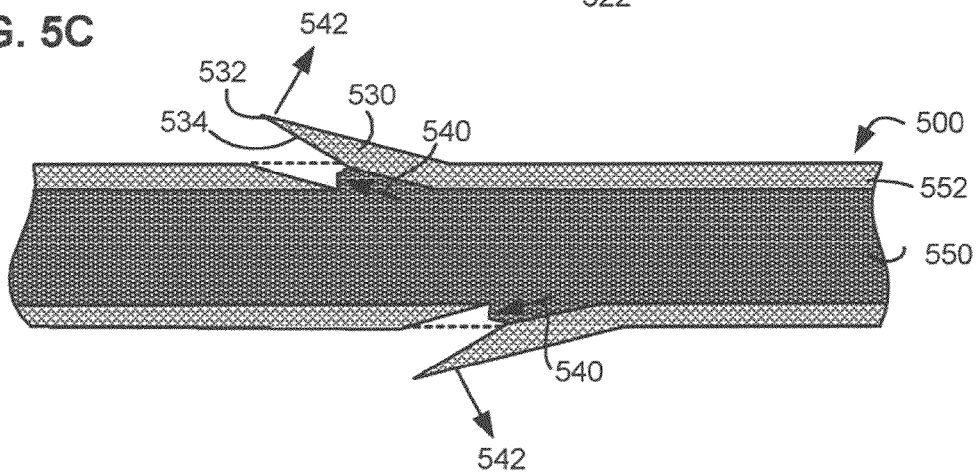

Referring now to FIG. 5C which shows a third example of a self-elevating retainer on a composite filament. In this example two materials have been used, a sheath material 552 and core material 550. In this example, core material 550 has been selected such that it expands slightly upon exposure to water. For example, partly deacetylated poly vinyl alcohol and lightly-cross-linked polyacrylic acid are polymers which expand upon contact with water. Thus, when filament 500 is exposed to moisture either by soaking the filament in water after retainer formation or by introducing the filament into a patient, then the core material expands as shown by arrow 540. Sheath material 552 is selected so that it does not expand when exposed to moisture. Thus, when the suture is exposed to moisture, core 550 expands in the direction of arrows 540 while sheath 552 does not expand. Expansion of the core causes the retainers 530 to elevate from the position shown by the dotted line to the position shown in FIG. 5C in the direction of arrows 542. Thus, in this example, the retainers 530 elevate themselves without mechanical intervention after exposing the filament 500, for example, to water or moisture either before or after introducing the suture into the tissues of a patient. In alternative embodiments other core materials may be selected having other physical and/or chemical triggers which cause them to expand. For example, thermoresponsive chitosan salts such as chitosan glycerophosphate undergo physical changes upon exposure to temperature.

G. Clinical Uses

In addition to the general wound closure and soft tissue repair applications, self-retaining sutures can be used in a variety of other indications.

Self-retaining sutures described herein may be used in various dental procedures, i.e., oral and maxillofacial surgical procedures and thus may be referred to as "self-retaining dental sutures." The above-mentioned procedures include, but are not limited to, oral surgery (e.g., removal of impacted or broken teeth), surgery to provide bone augmentation, surgery to repair dentofacial deformities, repair following trauma (e.g., facial bone fractures and injuries), surgical treatment of odontogenic and non-odontogenic tumors, reconstructive surgeries, repair of cleft lip or cleft palate, congenital craniofacial deformities, and esthetic facial surgery. Self-retaining dental sutures may be degradable or non-degradable, and may typically range in size from USP 2-0 to USP 6-0.

Self-retaining sutures described herein may also be used in tissue repositioning surgical procedures and thus may be referred to as "self-retaining tissue repositioning sutures". Such surgical procedures include, without limitation, face lifts, neck lifts, brow lifts, thigh lifts, and breast lifts. Self-retaining sutures used in tissue repositioning procedures may vary depending on the tissue being repositioned; for example, sutures with larger and further spaced-apart retainers may be suitably employed with relatively soft tissues such as fatty tissues.

Self-retaining sutures described herein may also be used in microsurgical procedures that are performed under a surgical microscope (and thus may be referred to as "self-retaining microsutures"). Such surgical procedures include, but are not limited to, reattachment and repair of peripheral nerves, spinal microsurgery, microsurgery of the hand, various plastic microsurgical procedures (e.g., facial reconstruction), microsurgery of the male or female reproductive systems, and various types of reconstructive microsurgery. Microsurgical reconstruction is used for complex reconstructive surgery problems when other options such as primary closure, healing by secondary intention, skin grafting, local flap transfer, and distant flap transfer are not adequate. Self-retaining microsutures have a very small caliber, often as small as USP 9-0 or USP 10-0, and may have an attached needle of corresponding size. The microsutures may be degradable or non-degradable.

Self-retaining sutures as described herein may be used in similarly small caliber ranges for ophthalmic surgical procedures and thus may be referred to as "ophthalmic self-retaining sutures". Such procedures include but are not limited to keratoplasty, cataract, and vitreous retinal microsurgical procedures. Ophthalmic self-retaining sutures may be degradable or non-degradable, and have an attached needle of correspondingly-small caliber.

Self-retaining sutures can be used in a variety of veterinary applications for a wide number of surgical and traumatic purposes in animal health.

Although the present invention has been shown and described in detail with regard to only a few exemplary embodiments of the invention, it should be understood by those skilled in the art that it is not intended to limit the invention to the specific embodiments disclosed. Various modifications, omissions, and additions may be made to the disclosed embodiments without materially departing from the novel teachings and advantages of the invention, particularly in light of the foregoing teachings. Accordingly, it is intended to cover all such modifications, omissions, additions, and equivalents as may be included within the spirit and scope of the invention as defined by the following claims.

What is claimed is:

1. A surgical suture comprising an elongated filament and a plurality of retainers wherein:
   the elongated filament is a composite filament including, a core portion formed of a first material and an sheath portion formed of a second material said plurality of retainers being formed in said sheath portion;

wherein the first material has higher tensile strength than the second material and where the first material comprises a material that expands when exposed to moisture, and wherein the second material is more easily plastically deformed than the first material and where the second material does not expand when exposed to moisture;

such that expansion of at least some of the core portion causes elevation of said plurality of retainers.

* * * * *